United States Patent
Miyazaki

(10) Patent No.: US 10,226,192 B2
(45) Date of Patent: *Mar. 12, 2019

(54) MAGNETIC RESONANCE IMAGING APPARATUS AND IMAGE PROCESSING APPARATUS

(71) Applicant: Toshiba Medical Systems Corporation, Tochigi-ken (JP)

(72) Inventor: Mitsue Miyazaki, Mount Prospect, IL (US)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 649 days.

This patent is subject to a terminal disclaimer.

(21) Appl. No.: 14/724,501

(22) Filed: May 28, 2015

(65) Prior Publication Data

US 2015/0257660 A1    Sep. 17, 2015

Related U.S. Application Data

(63) Continuation of application No. 11/896,941, filed on Sep. 6, 2007, now Pat. No. 9,134,394.

(30) Foreign Application Priority Data

Sep. 6, 2006  (JP) ................................ 2006-241574
Mar. 28, 2007 (JP) ................................ 2007-083840

(51) Int. Cl.
*A61B 5/05*    (2006.01)
*A61B 5/026*   (2006.01)
(Continued)

(52) U.S. Cl.
CPC .......... *A61B 5/0263* (2013.01); *A61B 5/0402* (2013.01); *A61B 5/055* (2013.01);
(Continued)

(58) Field of Classification Search
None
See application file for complete search history.

(56) References Cited

U.S. PATENT DOCUMENTS 5,830,143 A   11/1998  Mistretta et al.
6,144,201 A   11/2000  Miyazaki
(Continued)

FOREIGN PATENT DOCUMENTS

JP   2000-005144   1/2000
JP   2001-149341   6/2001
(Continued)

OTHER PUBLICATIONS

Miyazaki, et al., "Peripheral MR Angiography: Separation of Arteries from Veins with Flow-spoiled Gradient Pulses in Electrocardiography-triggered Three-dimensional Half-Fourier Fast Spin-Echo Imaging," *Radiology*, vol. 227, pp. 890-896 (2003).
(Continued)

*Primary Examiner* — Joel F Brutus
(74) *Attorney, Agent, or Firm* — Nixon & Vanderhye P.C.

(57) ABSTRACT

A magnetic resonance imaging apparatus includes a first data acquisition unit, a second data acquisition unit and an image data generating unit. The first data acquisition unit acquires first data from a slice to be a target after a first delay time from a reference of a first heart rate in synchronized with an electrocardiogram. The second data acquisition unit acquires second data from the slice after a second delay time from a reference of a second heart rate which is different from the first heart rate. The image data generating unit generates image data with image reconstruction processing using the first data and the second data.

4 Claims, 13 Drawing Sheets

(51) Int. Cl.
- *A61B 5/055* (2006.01)
- *A61B 5/00* (2006.01)
- *G01R 33/483* (2006.01)
- *G01R 33/563* (2006.01)
- *G01R 33/567* (2006.01)
- *A61B 5/0402* (2006.01)
- *G01R 33/561* (2006.01)

(52) U.S. Cl.
CPC ........ *A61B 5/7285* (2013.01); *G01R 33/4835* (2013.01); *G01R 33/5635* (2013.01); *G01R 33/5673* (2013.01); *A61B 5/004* (2013.01); *A61B 5/0044* (2013.01); *G01R 33/4838* (2013.01); *G01R 33/5611* (2013.01)

(56) References Cited

U.S. PATENT DOCUMENTS

| | | |
|---|---|---|
| 6,782,286 B2 | 8/2004 | Miyazaki |
| 6,801,800 B2 | 10/2004 | Miyazaki et al. |
| 6,954,068 B1 | 10/2005 | Takamori et al. |
| 7,545,967 B1 | 6/2009 | Prince et al. |
| 7,941,204 B1 | 5/2011 | Wang et al. |
| 2002/0021128 A1 | 2/2002 | Kuhara |
| 2003/0171671 A1 | 9/2003 | Miyazaki |
| 2004/0059213 A1 | 3/2004 | Kassai et al. |
| 2008/0071166 A1 | 3/2008 | Miyazaki |
| 2008/0081987 A1 | 4/2008 | Miyazaki |

FOREIGN PATENT DOCUMENTS

| | | |
|---|---|---|
| JP | 2002-010992 | 1/2002 |
| JP | 2002-200054 | 7/2002 |
| JP | 2003-70766 | 3/2003 |
| JP | 2003-135429 A | 5/2003 |
| JP | 2003-135430 | 5/2003 |
| JP | 2003-334177 A | 11/2003 |
| JP | 2004-329613 | 11/2004 |
| JP | 2004-329614 | 11/2004 |
| JP | 2006-130116 | 5/2006 |
| WO | 2006-028015 A1 | 3/2006 |

OTHER PUBLICATIONS

Miyazaki et al., "Non-Contrast-Enhanced MR Angiography Using 3D ECG-Synchronized Half-Fourier Fast Spin Echo," Journal of Magnetic Resonance Imagining, 12:776-783 (2000).
Chinese Office Action in CN Application 2007101045851 dated Oct. 30, 2009.
Office Action in U.S. Appl. No. 11/896,942 dated Sep. 6, 2007.
Japanese Office Action in counterpart JP 2007-092643 dated May 22, 2012.
Japanese Office Action in counterpart JP 2007-083840 dated May 29, 2012.
Japanese Office Action in counterpart JP 2012-162336 dated Feb. 12, 2014.
Office Action in U.S. Appl. No. 11/896,941 dated Aug. 3, 2010.
Office Action in U.S. Appl. No. 11/896,941 dated Mar. 23, 2011.
Office Action in U.S. Appl. No. 11/896,941 dated Oct. 11, 2011.
Office Action in U.S. Appl. No. 11/896,941 dated Jan. 9, 2013.
Office Action in U.S. Appl. No. 11/896,941 dated Oct. 25, 2013.
Office Action in U.S. Appl. No. 11/896,941 dated May 9, 2014.
Office Action in U.S. Appl. No. 11/896,941 dated Sep. 11, 2014.

NON-CONTRAST TIME-RESOLVED MRDSA

IMAGING CONDITION

ECHOSHARE MODE ◎ ON ○ OFF
PARALLEL IMAGING ◎ ON ○ OFF
NUMBER OF COILS [4]
NO WRAP [1.5]

PULSE SEQUENCE

| 2D FASE |
| 2D FASE WITH PARTIAL FS, FC |
| 3D FASE |
| 3D FASE WITH PARTIAL FS, FC |
| 2D FSE |
| 2D EPI |

DELAY TIME
INITIAL VALUE [100] ms
INCREMENT VALUE [5] ms
NUMBER OF PHASES [30] SHOT

IMAGE PROCESSING
AUTO SUBTRACTION ◎
AUTO MIP (3D) ○

IMAGE DISPLAY (3D)
PHASE/SWING ○
SWING/PHASE ○
NUMBER OF PROJECTION PLANES [4]
SPEED OF DISPLAY

MAGNETIC RESONANCE IMAGING APPARATUS AND IMAGE PROCESSING APPARATUS

CROSS-REFERENCE TO RELATED APPLICATIONS

This is a continuation U.S. Ser. No. 11/896,941 filed Sep. 6, 2007, which claims priority based on Japanese Patent Application Nos. 2006-241574 and 2007-083840 filed Sep. 6, 2006, and Mar. 28, 2007, respectively, the entire contents of all of which are hereby incorporated by reference herein. This application is related to U.S. Ser. No. 12/857,784 filed Aug. 17, 2010, now U.S. Pat. No. 8,577,443 issued Oct. 16, 2013, which is a divisional of U.S. Ser. No. 11/896,941. U.S. Ser. No. 11/896,942 filed Sep. 6, 2007 (now U.S. Pat. No. 9,194,928 issued Nov. 24, 2015), is also related hereto.

BACKGROUND OF THE INVENTION

1. Field of the Invention

The present invention relates to a magnetic resonance imaging (MRI) apparatus and an image processing apparatus which excite nuclear spin of an object magnetically with a RF (radio frequency) signal having the Larmor frequency and reconstruct an image based on an NMR (nuclear magnetic resonance) signal generated due to the excitation, and more particularly, to a magnetic resonance imaging apparatus and an image processing apparatus which can obtain a blood flow image in a shorter period of time without a contrast medium.

2. Description of the Related Art

Magnetic resonance imaging is an imaging method which excites nuclear spin of an object set in a static magnetic field with an RF having the Lamor frequency magnetically and reconstruct an image based on an NMR signal generated due to the excitation.

An MRA (Magnetic Resonance Angiography) is known as a technique for obtaining a blood flow image in a field of magnetic resonance imaging. An MRA without using contrast medium is called a non-contrast-enhanced MRA. In a non-contrast-enhanced MRA, a fresh blood imaging (FBI) method is designed, which clearly images a blood vessel by acquiring a high-velocity blood flow pumped out from a heart with ECG (electro cardiogram) synchronization (see, for example, Japanese Patent Application (Laid-Open) No. 2000-5144).

A non-contrast-enhanced MRA under the FBI method can obtain an MRA image with arteriovenous separation by obtaining a difference between pieces of image data acquired with varying delay times of ECG synchronization. Additionally, the Flow-Spoiled FBI method is designed, which suppresses an artery signal during systole by applying a spoiler pulse in the FBI method. The Flow-Spoiled FBI method images a difference between artery signals in diastole and systole of a myocardium. An ECG-prep scan to decide the optimum delay time of ECG synchronization is designed.

Furthermore, in the FBI method, the Flow-dephasing method is designed in order to image a low-velocity blood flow, which applies a gradient pulse (Gspoil) in a readout (RO) direction and adds a dephasing pulse or a rephasing pulse to a gradient magnetic field pulse (see, for example, Japanese Patent Application (Laid-Open) No. 2002-200054, Japanese Patent Application (Laid-Open) No. 2003-135430 and U.S. Pat. No. 6,801,800). The Flow-dephasing method can increase a relative signal difference between a high-velocity blood flow and a low-velocity blood flow by operation of a dephasing pulse or a rephasing pulse. Then, the relative signal difference allows to separate clearly arteries from veins.

This means it is important to enlarge a signal difference in a diastole and a systole for clear arteriovenous separation. In order to do this, it is necessary to reduce an intensity of a signal from a high-velocity blood flow in a systole. Therefore, a gradient pulse having an appropriate intensity in an RO direction is set and a blood flow signal from an artery in a systole is suppressed by the set gradient pulse. In this state, a blood flow signal in a diastole is acquired. Then, subtraction processing and/or maximum intensity projection (MIP) processing is performed to the blood flow signal acquired in the diastole and thus only arteries are imaged.

The Flow-prep. Scan is designed, which performs a preparation scan with changing parameters including an intensity of a dephasing pulse in an RO direction in the Flow-dephasing method (see, for example, Japanese Patent Application (Laid-Open) No. 2003-70766). The Flow-prep. Scan makes it possible to obtain the optimum parameter by referencing images acquired with changing a parameter by the preparation scan. A report of research about an intensity of a dephasing pulse in an RO direction has been made (see, for example, Miyazaki M, et al., Radiology 227:890-896, 2003).

An echoshare technique with the use of the Half-Fourier method is designed to obtain a blood flow image in a shorter scanning time (see, for example, Japanese Patent Application (Laid-Open) No. 2001-149341). Scans in a diastole and a systole obtain pieces of data respectively by this technique. By the scan in the systole, only echo data in a low-frequency region important for improving contrast is acquired in a short data acquisition time. Instead, copies of data in a high-frequency region acquired by the scan in the diastole are used as data in the high-frequency region that are not acquired in the systole. Moreover, data in insufficient region even with using copy of data in the diastole is calculated from each K-space data for the diastole and the systole by the Half-Fourier method to be used for image reconstruction.

A technique to obtain dynamic information of a blood flow simply without contrast medium and measuring a ECG-synchronization timing by an ECG-prep scan is designed (see, for example, Japanese Patent Application (Laid-Open) No. 2004-329614). This technique uses an ECG-prep scan as an imaging scan. Specifically, as in the case of an ECG-prep scan, dynamic information of a blood flow can be obtained by performing subtraction processing to pieces of two-dimensional data acquired more than once by an imaging scan with changing a delay time gradually from an R wave of an ECG signal.

FIG. 18 is a diagram showing a conventional imaging scan with use of an ECG-prep scan.

In FIG. 18, the abscissa denotes time. As shown in FIG. 18, a trigger signal is set initially at a timing of delay time d1 from an R wave of an ECG signal. Then, a scan for data acquisition is started in synchronized with the trigger signal. Then, a trigger signal is set at a timing of delay time d2 from an R wave of the ECG signal after completion of the scan for data acquisition. Then, a scan for data acquisition is started in synchronized with the trigger signal. In the same way, trigger signals are set at timings of delay times d3, d4, . . . from R waves of the ECG signal respectively, and a scan for data acquisition is started at a different timing in synchronized with each trigger signal. At this time, delay times d1, d2, . . . are set to be changed gradually in a systole of a myocardium showing a great change in velocity of a blood flow.

A pulse sequence that consists of a two-dimensional partial FS (flow spoiling) pulse and/or a two-dimensional partial FC (flow compensation) pulse is used as a scan for data acquisition.

The imaging scan as shown in FIG. 18 can reconstruct multiple pieces of image data each corresponding to a mutually different delay time from an R wave of the ECG signal.

FIG. 19 is a diagram showing delay times from an R wave of an ECG signal for respective acquisition timings of pieces of image data acquired by the imaging scan shown in FIG. 18.

In FIG. 19, the abscissa denotes time and each arrow denotes a timing of an R wave of an ECG signal. As shown in FIG. 19, multiple pieces of image data each corresponding to a mutually different delay time from an R wave of the ECG signal are generated by an imaging scan. This means multiple pieces of image data each corresponding to a mutually different cardiac time phase are generated. A subtraction image obtained by performing subtraction processing to the pieces of image data generated in this way becomes a blood flow image presenting dynamic information of a blood flow. This blood flow image is called the Time-resolved MRDSA (magnetic resonance digital subtraction angiography) image since it is a subtraction image of a blood flow resolved by time.

A technique is also designed to obtain dynamic information of a blood flow mentioned above by PI (parallel imaging) which is one of high speed imaging methods. PI is a technique for using a PAC (phased array coil) having surface coils as an RF coil for data reception (see, for example, Japanese Patent Application (Laid-Open) No. 2004-329613). By using PI for obtaining dynamic information of a blood flow, a scanning time can be reduced.

In the conventional technique for obtaining a Time-resolved MRDSA image, data acquisition time per 1 shot to acquire Time-resolved MRDSA data used for generating a Time-resolved MRDSA image is considerably long in view of an interval between R waves. Therefore, a TR (repetition time) is set to be about 3RR corresponding to 3 times of a distance RR between R waves.

Consequently, an imaging time of about 60 to 90 seconds is necessary to generate different Time-resolved MRDSA images corresponding to 20 to 30 time phases. Therefore, shortening of imaging time is needed.

In addition to shortening of imaging time, when scanned data is processed simply and appropriately in accordance with the diagnostic purpose and a user can refer to a diagnostic image more easily, working time and diagnostic time of the user can be reduced even if an imaging time might increase.

SUMMARY OF THE INVENTION

The present invention has been made in light of the conventional situations, and it is an object of the present invention to provide a magnetic resonance imaging apparatus and an image processing apparatus which make it possible to perform imaging such as non-contrast-enhanced MRA with a shorter imaging time.

Furthermore, another object of the present invention is to provide a magnetic resonance imaging apparatus and an image processing apparatus which make it possible to display a diagnostic image, such as an MRA image, appropriate for diagnosis with an easier operation by a user.

The present invention provides a magnetic resonance imaging apparatus comprising: a first data acquisition unit configured to acquire first data from a slice to be a target after a first delay time from a reference of a first heart rate in synchronized with an electrocardiogram; a second data acquisition unit configured to acquire second data from the slice after a second delay time from a reference of a second heart rate which is different from the first heart rate; and an image data generating unit configured to generate image data with image reconstruction processing using the first data and the second data, in an aspect to achieve an object.

The present invention also provides a magnetic resonance imaging apparatus comprising: a three-dimensional image data acquisition unit configured to acquire pieces of echo data with mutually different delay times from corresponding references of heart rate with regard to plural slices and generate plural pieces of three-dimensional image data respectively corresponding to the delay times by image reconstruction processing; a subtraction processing unit configured to generate three-dimensional blood flow image data by performing subtraction processing to the plural pieces of the three-dimensional image data; a projection unit configured to generate projection image data by performing projection processing to the three-dimensional blood flow image data; and an interface unit configured to set an image processing condition with an operation of an input device through a window displayed on a monitor so as to make at least one of the subtraction processing and the projection processing automatically performed after acquisition of the pieces of the echo data, in an aspect to achieve an object.

The present invention also provides a magnetic resonance imaging apparatus comprising: a three-dimensional image data acquisition unit configured to acquire pieces of echo data with mutually different delay times from corresponding references of heart rate with regard to plural slices and generate plural pieces of three-dimensional image data respectively corresponding to the delay times by image reconstruction processing; a subtraction processing unit configured to generate time-series three-dimensional blood flow image data by performing subtraction processing to the plural pieces of the three-dimensional image data; a projection unit configured to generate time-series pieces of projection image data corresponding to plural projection directions respectively by performing projection processing in the plural projection directions to the time-series three-dimensional blood flow image data; an interface unit configured to set which of a first display order and a second display order the time-series pieces of the projection image data are displayed by with an operation of an input device through a window displayed on a monitor, the first display order being one by which the time-series pieces of the projection image data are displayed sequentially according to progress of time phase and subsequently displayed sequentially with changing a projection direction, the second display order being one by which pieces of projection image data with changing the projection direction are displayed sequentially and subsequently pieces of projection image data of next time phase are displayed sequentially; and a display unit configured to display the time-series pieces of the projection image data according to a display order set by said interface unit, in an aspect to achieve an object.

The present invention also provides a magnetic resonance imaging apparatus comprising: a data acquisition unit configured to acquire corresponding pieces of data in mutually different heart rates respectively by a sequence for noncontrast-enhanced MRA in synchronized with an electrocardiogram; and an image data generating unit configured to generate non-contrast-enhanced MRA image data from the pieces of the data, in an aspect to achieve an object.

The present invention also provides an image processing apparatus comprising: a first image data acquisition unit configured to acquire first image data acquired from a slice to be a target after a first delay time from a reference of a first heart rate in synchronized with an electrocardiogram; a second data acquisition unit configured to acquire second image data acquired from the slice after a second delay time from a reference of a second heart rate which is different from the first heart rate; and an image data generating unit configured to generate third image data using the first image data and the second image data, in an aspect to achieve an object.

The present invention also provides an image processing apparatus comprising: a three-dimensional image data acquisition unit configured to acquire plural pieces of three-dimensional image data generated with image reconstruction processing to pieces of echo data acquired with mutually different delay times from corresponding references of heart rate with regard to plural slices, the plural pieces of the three-dimensional image data corresponding to the delay times respectively; a subtraction processing unit configured to generate three-dimensional blood flow image data by performing subtraction processing to the plural pieces of the three-dimensional image data; a projection unit configured to generate projection image data by performing projection processing to the three-dimensional blood flow image data; and an interface unit configured to set an image processing condition with an operation of an input device through a window displayed on a monitor so as to make at least one of the subtraction processing and the projection processing automatically performed after acquisition of the plural pieces of the three-dimensional image data, in an aspect to achieve an object.

The present invention also provides an image processing apparatus comprising: a three-dimensional image data acquisition unit configured to acquire plural pieces of three-dimensional image data generated with image reconstruction processing to pieces of echo data acquired with mutually different delay times from corresponding references of heart rate with regard to plural slices, the plural pieces of the three-dimensional image data corresponding to the delay times respectively; a subtraction processing unit configured to generate time-series three-dimensional blood flow image data by performing subtraction processing to the plural pieces of the three-dimensional image data; a projection unit configured to generate time-series pieces of projection image data corresponding to plural projection directions respectively by performing projection processing in the plural projection directions to the time-series three-dimensional blood flow image data; an interface unit configured to set which of a first display order and a second display order the time-series pieces of the projection image data are displayed by with an operation of an input device through a window displayed on a monitor, the first display order being one by which the time-series pieces of the projection image data are displayed sequentially according to progress of time phase and subsequently displayed sequentially with changing a projection direction, the second display order being one by which pieces of projection image data with changing the projection direction are displayed sequentially and subsequently pieces of projection image data of next time phase are displayed sequentially; and a display unit configured to display the time-series pieces of the projection image data according to a display order set by said interface unit, in an aspect to achieve an object.

The present invention also provides an image processing apparatus comprising: an image data acquisition unit configured to acquire pieces of data acquired in mutually different heart rates respectively by a sequence for non-contrast-enhanced MRA in synchronized with an electrocardiogram, the pieces of the data corresponding to the mutually different heart rates respectively; and a non-contrast-enhanced MRA image data generating unit configured to generate non-contrast-enhanced MRA image data from the pieces of the data, in an aspect to achieve an object.

The magnetic resonance imaging apparatus and the image processing apparatus as described above make it possible to perform imaging such as non-contrast-enhanced MRA with a shorter imaging time.

Further, the magnetic resonance imaging apparatus and the image processing apparatus as described above make it possible to display a diagnostic image, such as an MRA image, appropriate for diagnosis with an easier operation by a user.

BRIEF DESCRIPTION OF THE DRAWINGS

In the accompanying drawings:

FIG. 6 is a diagram showing an example of setting window displayed as a user interface on the monitor shown in FIG. 1;

DESCRIPTION OF THE PREFERRED EMBODIMENTS

A magnetic resonance imaging apparatus and an image processing apparatus according to embodiments of the present invention will be described with reference to the accompanying drawings.

Figure 1:
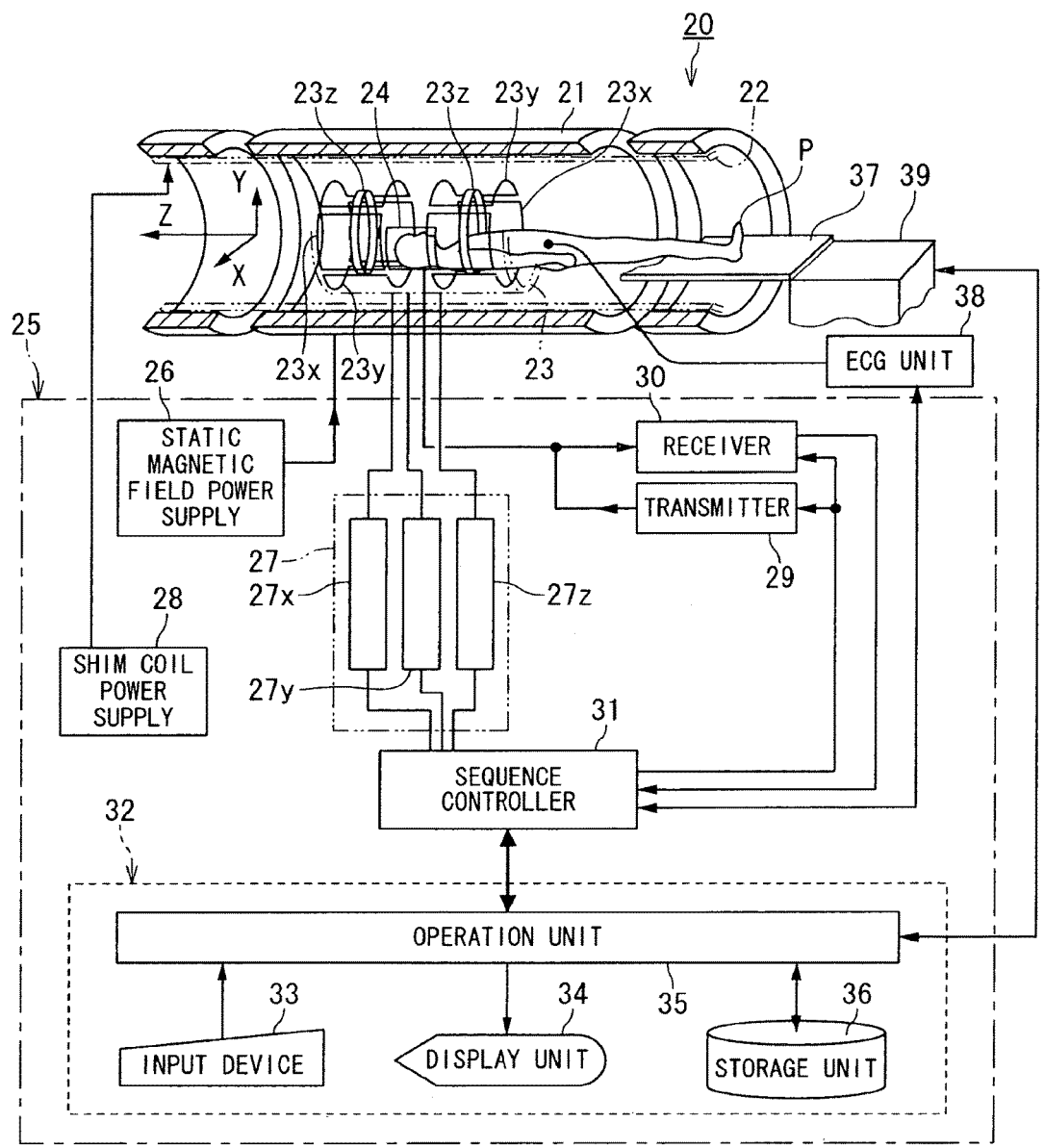
FIG. 1 is a block diagram showing a magnetic resonance imaging apparatus according to an embodiment of the present invention.

FIG. 1 is a block diagram showing a magnetic resonance imaging apparatus according to an embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil unit 23 and a RF coil 24. The static field magnet 21, the shim coil 22, the gradient coil unit 23 and the RF coil 24 are built in a gantry (not shown).

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a monitor 34, a operation unit 35 and a storage unit 36.

The static field magnet 21 communicates with the static magnetic field power supply 26. The static magnetic field power supply 26 supplies electric current to the static field magnet 21 to get the function to generate a static magnetic field in a imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil unit 23 includes an X-axis gradient coil unit 23x, a Y-axis gradient coil unit 23y and a Z-axis gradient coil unit 23z. Each of the X-axis gradient coil unit 23x, the Y-axis gradient coil unit 23y and the Z-axis gradient coil unit 23z which is cylinder-shaped is arranged inside the static field magnet 21. The gradient coil unit 23 has also a bed 37 in the area formed inside it which is an imaging area. The bed 37 supports an object P. Around the bed 37 or the object P, the RF coil 24 may be arranged instead of being built in the gantry.

The gradient coil unit 23 communicates with the gradient power supply 27. The X-axis gradient coil unit 23x, the Y-axis gradient coil unit 23y and the Z-axis gradient coil unit 23z of the gradient coil unit 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil unit 23x, the Y-axis gradient coil unit 23y and the Z-axis gradient coil unit 23z respectively so as to generate gradient magnetic fields Gx, Gy and Gz in the X, Y and Z directions in the imaging area.

The RF coil 24 communicates with the transmitter 29 and the receiver 30. The RF coil 24 has a function to transmit a RF signal given from the transmitter 29 to the object P and receive an NMR signal generated due to nuclear spin inside the object P which is excited by the RF signal to give to the receiver 30.

Figure 2:
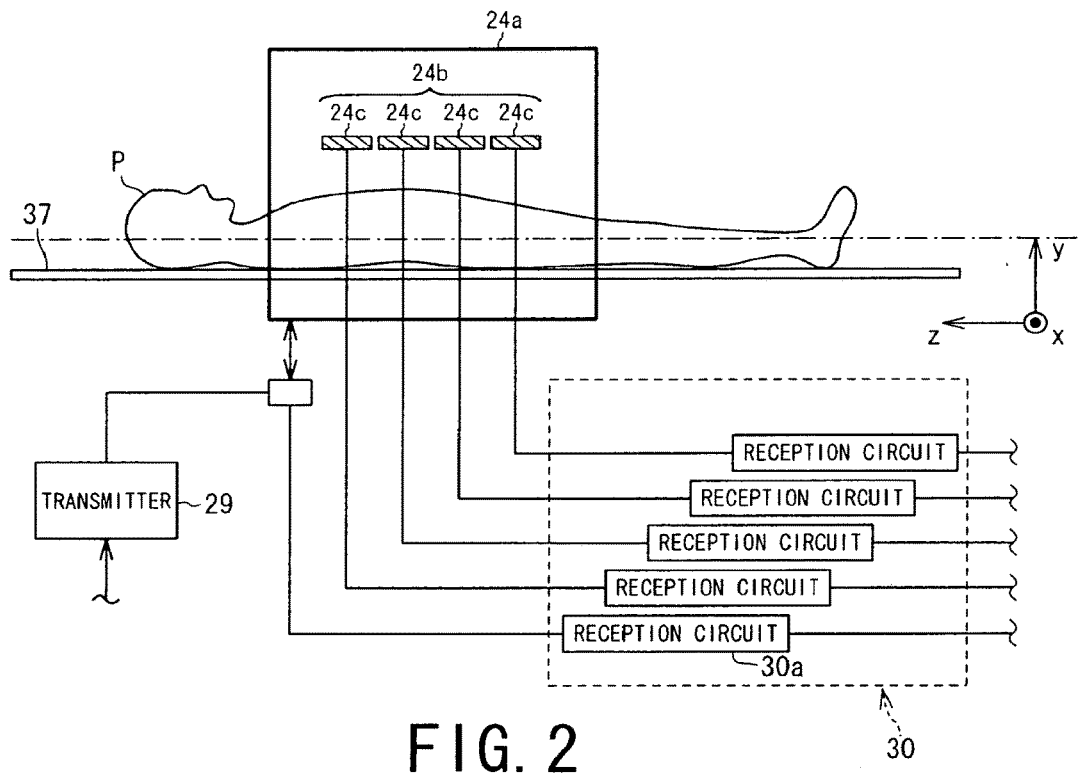
FIG. 2 is a diagram showing an example of detail structure of the RF coil shown in FIG. 1.
Figure 3:
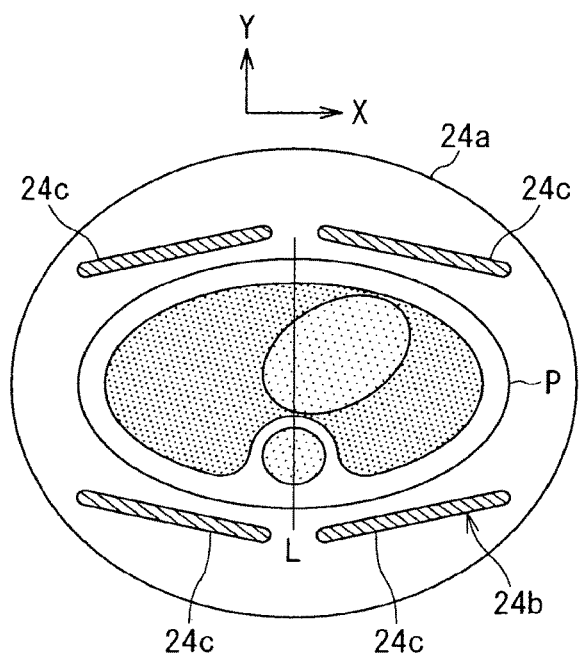
FIG. 3 is a sectional illustration showing an example arrangement of the WB coil and the phased array coils shown in FIG. 2.

FIG. 2 is a diagram showing an example of detail structure of the RF coil 24 shown in FIG. 1. FIG. 3 is a sectional illustration showing an example arrangement of the WB coil 24a and the phased array coils 24b shown in FIG. 2.

The RF coil 24 is structured by a transmission RF coil 24 and a reception RF coil 24, for example. The transmission RF coil 24 uses a whole-body (WB) coil 24a while the reception RF coil 24 uses a phased array coil 24b. The phased array coil 24b has a plurality of surface coils 24c. The surface coils 24c are separately connected to respective reception circuits 30a.

Meanwhile, the surface coils 24c of the phased array coil 24b are arranged, symmetric about the Z-axis, in peripheral regions of a section L including a particular region of interest in the object P for example. Furthermore, the WB coil 24a is provided at the outer of the phased array coil 24b. Thus, a radio frequency signal can be transmitted to the object P by the WB coil 24a while an NMR signal of from the section L including the particular region of interest can be received at multi-channels by the WB coil 24a or the surface coils 24c of the phased array coil 24b and provided to the reception circuits 30a of the receiver 30.

However, the RF coil 24 may be structured by desired coils suited for various applications or by a single coil.

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27

The sequence controller 31 is also configured to give raw data to the computer 32. The raw data is complex number data obtained through the detection of an NMR signal and A/D conversion to the NMR signal detected in the receiver 30.

The transmitter 29 has a function to give a RF signal to the RF coil 24 in accordance with control information provided from the sequence controller 31. The receiver 30 has a function to generate raw data which is digitized complex number data by detecting a NMR signal given from the RF coil 24 and performing predetermined signal processing and A/D converting to the NMR signal detected. The receiver 30 also has a function to give the generated raw data to the sequence controller 31.

In addition, an ECG unit 38 for acquiring an ECG signal of the object P is provided with the magnetic resonance imaging apparatus 20. The ECG signal detected by the ECG unit 38 is outputted to the computer 32 through the sequence controller 31.

Furthermore, the bed 37 is provided with a table drive unit 39. The table drive unit 39 is connected with the computer 32 so as to move the table of the bed 37 under the control by the computer 32 for imaging with moving table method or stepping table method. The moving table method is a technique for obtaining a large FOV (field of view) in a moving direction by continuously moving the table of the bed 37 during imaging. The stepping table method is a technique for three-dimensional imaging at every station by stepping the table of the bed 37. These techniques are used in case of imaging a large area which is unable to be imaged at a time such as whole body imaging. The images acquired with moving the bed 37 may be combined mutually by compound processing in the computer 32.

The computer 32 gets various functions by the operation unit 35 executing some programs stored in the storage unit 36 of the computer 32. Alternatively, some functions may be provided with the magnetic resonance imaging apparatus 20 by some specific circuits instead of using some of the programs.

Figure 4:
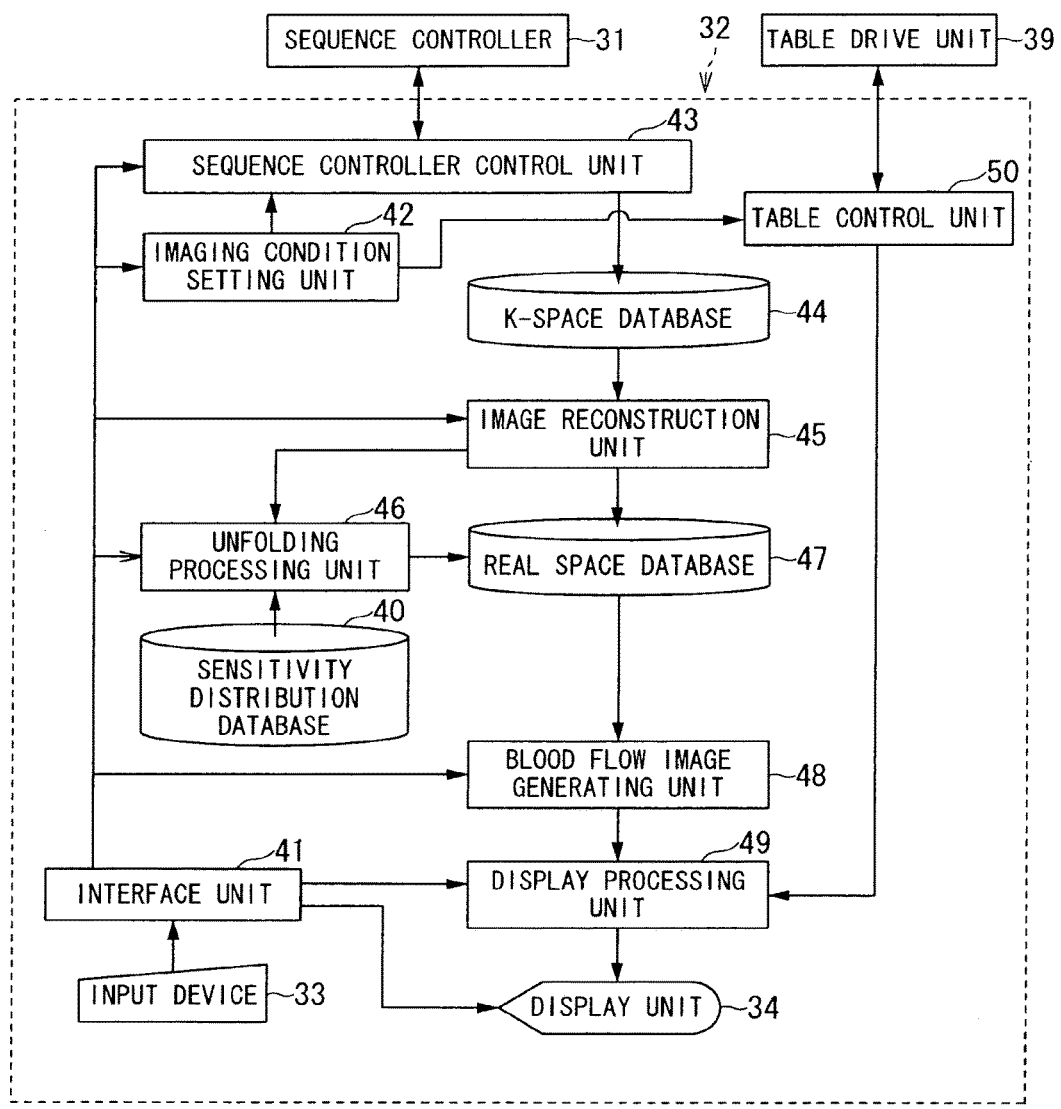
FIG. 4 is a functional block diagram of the computer shown in FIG. 1.

FIG. 4 is a functional block diagram of the computer 32 shown in FIG. 1.

The computer 32 functions as a sensitivity distribution database 40, an interface unit 41, an imaging condition setting unit 42, a sequence controller control unit 43, a k-space database 44, an image reconstruction unit 45, an unfolding processing unit 46, a real space database 47, a blood flow image generating unit 48, a display processing unit 49 and a table control unit 50 by program.

The sensitivity distribution database 40 stores each sensitivity distribution of the surface coils 24c included in the phased array coil 24b.

The interface unit 41 has a function to display a window for setting and inputting various information on the display unit 34 with the GUI (Graphical User Interface) technology and a function to receive instruction from the input device 33 and provide it to corresponding components. Information such as an imaging condition, an image processing method and an image displaying method can be cited as set information.

Sequences for non-contrast MRA each to be set as an imaging condition includes two-dimensional or three-dimensional FSE (Fast spin echo) sequence, EPI (echo planar imaging) sequence, FASE (fast asymmetric spin echo) sequence and SSFP (steady state free precession) sequence. Using two-dimensional sequence make it possible to reduce imaging period. Further, in case of using two-dimensional FASE sequence, a Partial FS pulse or a Partial FC pulse for controlling a phase of magnetized spin may be added to a gradient magnetic field pulse in a RO (readout) direction according to a blood velocity.

An FASE sequence with applying a partial FC pulse is suitable for imaging a portion such as a vessel with a high-velocity blood flow. When imaging a portion showing a low-velocity blood flow, an FASE sequence with applying a flow spoiling pulse, an EPI sequence or an SSFP sequence can be used. Since an SSFP sequence has a long TE (echo time) and is sensitive to a flow, it can depict a flow-void image in a systole and/or a bright blood image in a diastole.

Further, a delay time from an R wave of an ECG signal and the number of data acquisition (the number of shots) are set as imaging conditions to generate a Time-resolved MRDSA image. For example, each delay time can be set as a delay time until the first data acquisition, i.e., an initial value of the delay time and an increment value indicating an amount of change of the delay time.

The set imaging conditions including the pulse sequence, the delay time and the number of shots are output from the interface unit 41 to the imaging condition setting unit 42 and the image reconstruction unit 45.

In addition, an imaging mode with the echoshare and/or an imaging mode under PI can be selected as an imaging condition for generating a Time-resolved MRDSA image. Imaging with the echoshare acquires only echo data in a low-frequency region critical for improvement of contrast in a short data acquisition time in a scan in a systole and uses a copy of data in a high-frequency region acquired in a scan in a diastole as data in the high-frequency region that was not acquired in the systole.

PI receives data with multiple surface coils 24c and reduces the number of phase encodes into a value obtained by multiplying the reciprocal of the number of the surface coil 24c with the number of phase encodes necessary for image reconstruction by skipping at least one phase encode. When the imaging mode under PI is selected, conditions specific to PI are also set. As conditions specific to PI, the number of the surface coil 24c used as a receiver coil and a ratio for expanding a FOV for unfolding processing, which is post-processing to image data obtained by PI, so that the FOV for unfolding processing becomes larger than that set at the time of an imaging plan in order to prevent folding possibly occurred in PI, are cited. The number of the surface coil 24c is also called the speeding-up rate.

When the imaging mode with echoshare is selected, instruction to set an imaging condition with echoshare is provided from the interface unit 41 to the image condition setting unit 42, and instruction to perform image reconstruction processing with echoshare together with necessary imaging condition information is provided from the interface unit 41 to the image reconstruction unit 45.

When the imaging mode under PI is selected, instruction to set an imaging condition for PI is provided from the interface unit 41 to the image condition setting unit 42. Further, information that a target of reconstruction processing is each piece of K-space data, acquired by PI, from the respective surface coils 24c is provided from the interface unit 41 to the image reconstruction unit 45, and a condition for PI is provided from the interface unit 41 to the unfolding processing unit 46 then used for unfolding processing.

Moreover, when imaging by the moving table method or the stepping-table method, instruction to set conditions including a position of the bed 37 and an amount of step is provided from the interface unit 41 to the image condition setting unit 42 as imaging conditions.

As image processing methods, instruction indicating whether to generate a blood flow image by automatically performing traction processing to reconstructed image data and/or instruction indicating whether to automatically perform projection processing such as MIP (maximum intensity projection) processing when a blood flow image is three-dimensional can be made. Instruction indicating automatic subtraction processing and/or automatic projection processing is provided from the interface unit 41 to the blood flow image generating unit 48.

In addition, as an image displaying method, when a blood flow image is each of time series projection images obtained by projection processing, conditions including a projecting direction, a display order and a display speed of the projection images can be appointed. The swing/phase display that displays multiple projection images while swinging a direction of projection and subsequently displays the projection images of the next phase, and inversely, the phase/swing display that displays multiple projection images while swinging the phase and subsequently displays the projection images swung in another direction are cited as a display order. However, only projection images projected in a constant direction can be displayed dynamically as an image displaying method.

When the swing/phase display or the phase/swing display is instructed through operation of the input device 33, instruction of projection images that should be generated is provided to the blood flow image generating unit 48, and a display order and/or a display speed of generated projection images are provided as instruction to the display processing unit 49, respectively from the interface unit 41.

When imaging by the moving table method or the stepping-table method, since multiple pieces of imaging data are obtained on every position of the bed 37, a displaying method of the imaging data at every position of the bed 37 can be specified. Instruction of the displaying method of the imaging data at every position of the bed 37 is provided from the interface unit 41 to the display processing unit 49.

The imaging condition setting unit 42 has a function to set imaging conditions including a pulse sequence according to instruction obtained from the input device 33 through the interface unit 41 and provide the set imaging conditions to the sequence controller control unit 43. When imaging by the moving table method or the stepping-table method, the imaging condition setting unit 42 is configured to provide control information of the bed 37 according to the imaging conditions to the table control unit 50.

The sequence controller control unit 43 has a function for controlling the driving of the sequence controller 31 by giving imaging condition information indicating imaging conditions including a pulse sequence obtained from the imaging condition setting unit 42 to the sequence controller 31 based on indication of starting a scan obtained from the input device 33 through the interface unit 41 or another element. Further, the sequence controller control unit 43 has a function for receiving raw data, which is k-space (Fourier space) data, from the sequence controller 31 and arranging the raw data to k space formed in the k-space database 44.

The k-space database 44 stores the k-space data received from the sequence controller control unit 43.

The image reconstruction unit 45 has a function for capturing the k-space data from the k-space database 44, generating image data from the k-space data by performing image reconstruction processing, such as Fourier transform processing to the k-space data, and writing the generated image data to the real space database 47. In addition, the image reconstruction unit 45 is configured to perform image reconstruction processing with echoshare according to instruction and imaging conditions when the instruction to perform image reconstruction processing with echoshare and the imaging conditions is provided from the interface unit 41.

Further, the image reconstruction unit 45 is also configured to provide pieces of image data from the respective surface coils 24c obtained by imaging with PI to the unfolding processing unit 46. Information about whether the imaging conditions include imaging under PI or not is provided through the interface unit 41 from the input device 33 to the image reconstruction unit 45.

The unfolding processing unit 46 has a function to generate unfolded image data by performing unfolding process, which is post-processing in PI, to image date from each surface coil 24c obtained from the image reconstruction unit 45 in accordance with the conditions for PI acquired from the interface unit 41 and also to write the generated image data in the real space database 47. The unfolding processing unit 46 is configured to be able to refer to the sensitivity distribution of each surface coil 24c stored in the sensitivity distribution database 40 for unfolding processing.

The real space database 47 stores image data generated by the image reconstruction unit 45 or the unfolding processing unit 46.

The blood flow image generating unit 48 has a function to acquire multiple pieces of image data each corresponding to a mutually different cardiac time phase stored in the real space database 47 to generate blood flow image data for displaying according to instruction from the interface unit 41. For example, by subtraction processing between pieces of image data each corresponding to a mutually near time phase or between reference image data and image data corresponding to each time phase, two-dimensional or three-dimensional Time-resolved MRDSA image data can be generated. Furthermore, blood flow image data for displaying can be generated by performing necessary image processing such as MIP processing in a predetermined direction to the Time-resolved MRDSA image data according to instruction from the interface unit 41. Note that, it is acceptable to consider image data in each time phase as blood flow image data for displaying without subtraction processing to image data.

The Blood flow image data such as two-dimensional Time-resolved MRSDA image data and projection image data finally generated for displaying is provided from the blood flow image generating unit 48 to the display processing unit 49.

The display processing unit 49 has a function to output the blood flow image data acquired from the blood flow image generating unit 48 on the display unit 34 at the displaying order and the displaying speed instructed by the interface unit 41. When imaging by the moving table method and the stepping-table method, the display processing unit 49 is configured to obtain the positional information of the bed 37 from the table control unit 50 and output blood flow image data, corresponding to each position of the bed 37, on the display unit 34 according to the displaying method instructed by the interface unit 41.

The table control unit 50 has a function to provide the positional information of the bed 37 to the table drive unit 39 to control the table drive unit 39 so that the bed 37 can drive according to the control information of the bed 37 depending on the imaging conditions provided by the imaging condition setting unit 42, and to provide the positional information of the bed 37 to the display processing unit 49.

Then, the operation and action of the magnetic resonance imaging apparatus 20 will be described.

Figure 5:
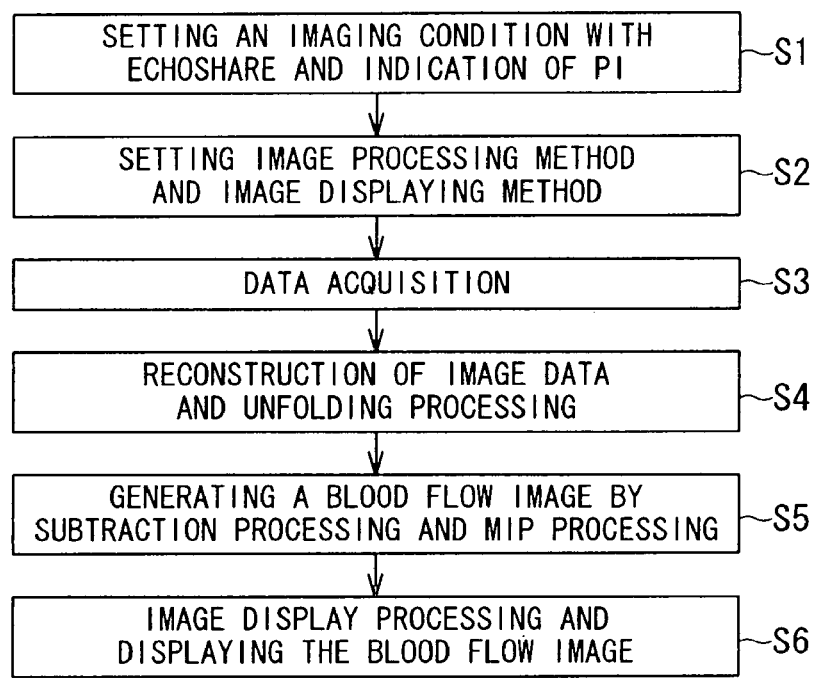
FIG. 5 is a flowchart showing a procedure for acquiring a non-contrast Time-resolved MRDSA image of the object with the magnetic resonance imaging apparatus shown in FIG. 1.

FIG. 5 is a flowchart showing a procedure for acquiring a non-contrast Time-resolved MRDSA image of the object P with the magnetic resonance imaging apparatus 20 shown in FIG. 1. The symbols including S with a number in FIG. 5 indicate each step of the flowchart.

In step S1, instruction of whether to apply echoshare and PI as imaging conditions for acquiring a non-contrast-enhanced Time-resolved MRDSA image is provided. For that purpose, window information is provided from the interface unit 41 to the display unit 34, and a setting window to set information including an imaging condition, an image processing condition, an image displaying condition and the like is displayed on the display unit 34.

FIG. 6 is a diagram showing an example of setting window displayed as a user interface on the monitor 34 shown in FIG. 1.

For example, a setting window to set an imaging condition, an image processing condition and an image displaying condition is displayed on the display unit 34 as shown in FIG. 6. The imaging mode with echoshare and/or the imaging mode under PI can be selected respectively as an imaging condition. FIG. 6 shows an example in which both of the echoshare mode and the PI mode are selected. Since the PI mode is selected, the number of the surface coil 24c and a No Wrap value indicating a scale for enlarging a FOV for unfolding processing to prevent folding are set respectively. FIG. 6 shows an example in which the number of the surface coil 24c for data acquisition is 4 and the No Wrap value is 1.5.

A pulse sequence for a non-contrast-enhanced MRA can be selected from preset candidates. FIG. 6 shows an example in which a two-dimensional FASE sequence is selected. Since data acquisition for a non-contrast-enhanced Time-resolved MRDSA image is performed over plural times with extending a delay time from an R wave of an ECG signal gradually, each delay time and the number of data acquisition, i.e., the number of shots are set. In FIG. 6, an initial delay time from an R wave for the first data acquisition and an increment value equivalent to an increment of a delay time for the following data acquisition are set to 100 ms and 5 ms, respectively. In addition, the number of shots is set to 30.

As shown in FIG. 6, "NUMBER OF PHASES" instead of "NUMBER OF SHOTS" may be displayed since a single shot sequence such as an FASE sequence which is an FSE sequence with using half Fourier method may be used.

When the imaging mode with echoshare is selected, the K-space data from the low-frequency region to the high-frequency region necessary for reconstruction of a slice of Time-resolved MRDSA image is acquired at least once, and an imaging condition is set so that only K-space data of the low-frequency region including data that is at least necessary for ensuring contrast is acquired in other data acquisition. The range of K-space data to be acquired in the low-frequency region can be determined by imaging on a trial basis in advance and determining whether the contrast can be sufficiently obtained or not.

For this reason, in the imaging mode with echoshare, the data acquisition time for acquiring the only K-space data in the low-frequency region can be decreased. Preferably, an imaging condition is set so that the K-space data in the low-frequency region is acquired between consecutive R waves of an ECG signal, i.e., in one heart beat. More preferably, an imaging condition is set so that a time necessary for a longitudinal relaxation (T1) recovery can be secured between the end of data acquisition and the next R wave.

From the viewpoint that the data acquisition time is made shorter and that the data in the high-frequency region is acquired as higher signal values, the data in the high-frequency region is acquired in the last data acquisition with the longest delay time for practical purposes. A case where the data from the low-frequency region to the high-frequency region is acquired only once in the last data acquisition is described here.

Figure 7:
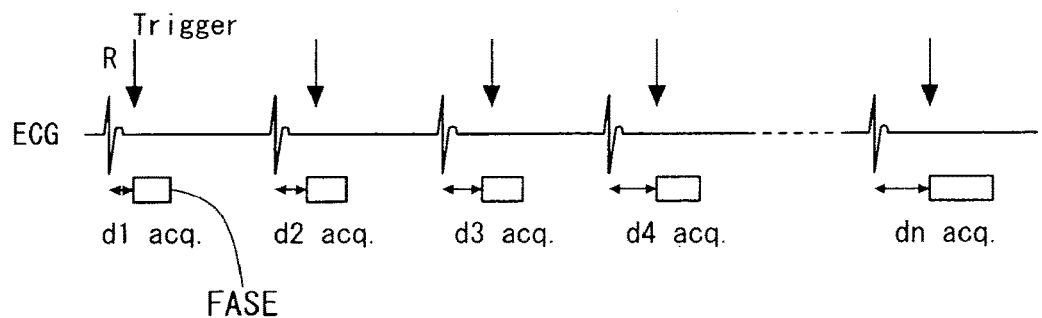
FIG. 7 is a diagram showing delay times for data acquisitions and data acquisition periods in case of selecting the echo share mode on the setting window shown in FIG. 6.

FIG. 7 is a diagram showing delay times for data acquisitions and data acquisition periods in case of selecting the echo share mode on the setting window shown in FIG. 6.

As shown in FIG. 7, the data acquisition time is reduced since the data only in the low-frequency region is acquired in each data acquisition other than the last data acquisition of nth. When an FASE sequence obtained by combining the fast SE method with the Half-Fourier method is selected as a sequence for the data acquisition, the data acquisition time can be reduced further and the data in the low-frequency region can be acquired in one heart beat.

Therefore, triggers can be set at timings of delay times d1, d2, d3, . . . , dn from R waves of an ECG signal respectively, and the data can be acquired continuously.

Figure 8:
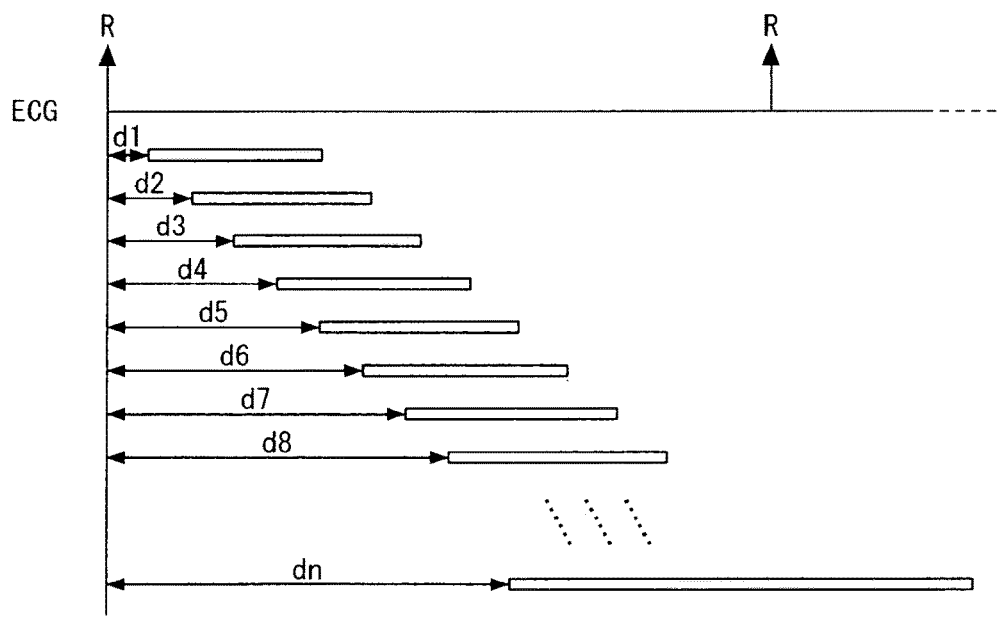
FIG. 8 is a diagram showing relation between pieces of data acquired by the data acquisition shown in FIG. 7.

FIG. 8 is a diagram showing relation between pieces of data acquired by the data acquisition shown in FIG. 7.

In FIG. 8, the abscissa denotes time and each arrow denotes a timing of an R wave of an ECG signal. By the data acquisition as shown in FIG. 7, multiple pieces of K-space data corresponding to mutually different delay times from R waves of the ECG signal as shown in FIG. 8 can be acquired. Since the nth K-space data includes both data in the low-frequency region and the high-frequency region, it has a data size larger than that of the K-space data acquired with another delay time. The image data can be generated from multiple pieces of K-space data corresponding to mutually different cardiac time phases as described above. Furthermore, a subtraction image obtained by subtraction processing to the generated pieces of image data becomes a Time-resolved MRDSA image that represents a dynamic state of a blood flow.

Figure 9:
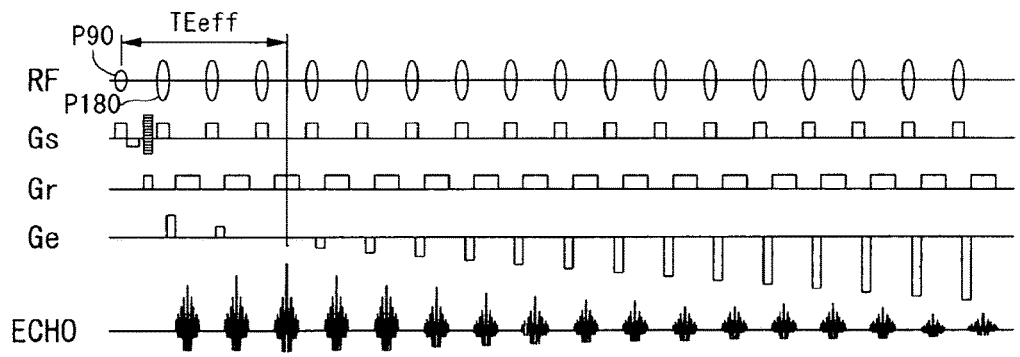
FIG. 9 is a diagram showing an FASE sequence used as a sequence for the data acquisition shown in FIG. 7.

FIG. 9 is a diagram showing an FASE sequence used as a sequence for the data acquisition shown in FIG. 7.

In FIG. 9, RF denotes RF signals to be transmitted, Gs denotes a gradient magnetic field for slice selection, Gr denotes a gradient magnetic field for readout, Ge denotes a gradient magnetic field for phase encode and ECHO denotes acquired echo data.

As shown in FIG. 9, following a 90 degrees excitation pulse P90, a 180 degrees refocus pulse P180 is continuously applied to an object P as an RF signal. In addition, gradient magnetic fields Gs, Gr, Ge for slice selection, for readout and for phase encoding are applied to the object P. In each data acquisition other than nth one, an RF signal and gradient magnetic fields are applied to the object P so that only echo data in the low-frequency region can be acquired. On the contrary, in the nth data acquisition, an RF signal and gradient magnetic fields are applied to the object P so that echo data in the high-frequency region as well as the low-frequency region can be acquired. Consequently, data in the center of K-space is acquired after the effective echo time TEeff.

A partial FC pulse and/or a partial FS pulse can be applied along with a gradient magnetic field pulse for readout depending on a velocity of a blood flow. Since a partial FC pulse and a partial FS pulse have a function to control a phase of magnetization spin, they can be called a phase behavioral control pulse.

Figure 10:
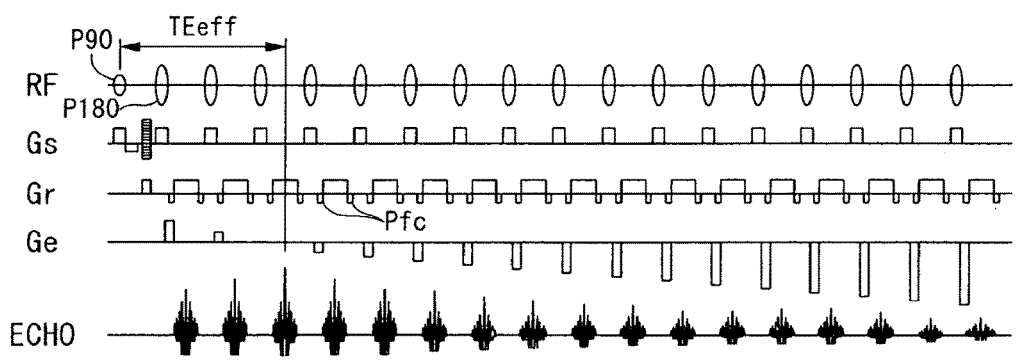
FIG. 10 is a diagram showing a sequence obtained by adding Partial FC pulses to the FASE sequence shown in FIG. 9.

FIG. 10 is a diagram showing a sequence obtained by adding Partial FC pulses to the FASE sequence shown in FIG. 9.

In FIG. 10, RF denotes RF signals to be transmitted, Gs denotes a gradient magnetic field for slice selection, Gr denotes a gradient magnetic field for readout, Ge denotes a gradient magnetic field for phase encode and ECHO denotes acquired echo data.

As shown in FIG. 10, a partial FC pulse Pfc is applied before and after a gradient magnetic field pulse for readout in the direction of the reverse polarity. The waveform area of the partial FC pulse Pfc is set to larger than 0% and smaller than 100% of that of the gradient magnetic field pulse for readout depending on a velocity of a blood flow. Then, by the operation of the partial FC pulse Pfc applied before the gradient magnetic field pulse for readout, phase dispersion of the magnetization spin is suppressed and thus the signal value can be acquired without fail. The partial FC pulse Pfc applied after the gradient magnetic field pulse for readout has a role to compensate the phase of the magnetization spin. For this reason, when a blood flow velocity is high and a signal value is low, the use of an FASE sequence with applying a partial FC pulse Pfc for imaging is effective.

Figure 11:
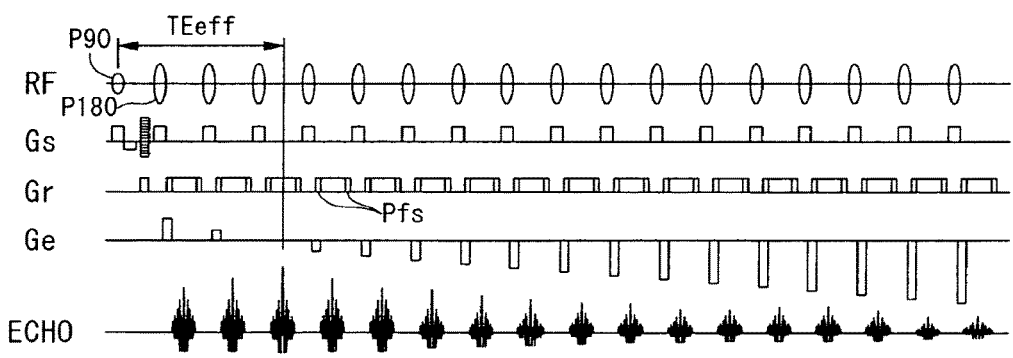
FIG. 11 is a diagram showing a sequence obtained by adding Partial FS pulses to the FASE sequence shown in FIG. 9.

FIG. 11 is a diagram showing a sequence obtained by adding Partial FS pulses to the FASE sequence shown in FIG. 9.

In FIG. 11, RF denotes RF signals to be transmitted, Gs denotes a gradient magnetic field for slice selection, Gr denotes a gradient magnetic field for readout, Ge denotes a gradient magnetic field for phase encode and ECHO denotes acquired echo data.

As shown in FIG. 11, a partial FS pulse Pfs is applied before and after a gradient magnetic field pulse for readout in the direction of the reverse polarity. The waveform area of the partial FS pulse Pfs is set to larger than 0% and smaller than 100% of that of the gradient magnetic field pulse for readout depending on a velocity of a blood flow. Then, by the operation of the partial FS pulse Pfs applied before the gradient magnetic field pulse for readout, phase dispersion of the magnetization spin is promoted and thus a high signal value can be acquired. The partial FS pulse Pfs applied after the gradient magnetic field pulse for readout has a role to compensate the phase of the magnetization spin. For this reason, when a blood flow velocity is low, the use of an FASE sequence with applying a partial FS pulse Pfs for imaging is effective.

Figure 12:
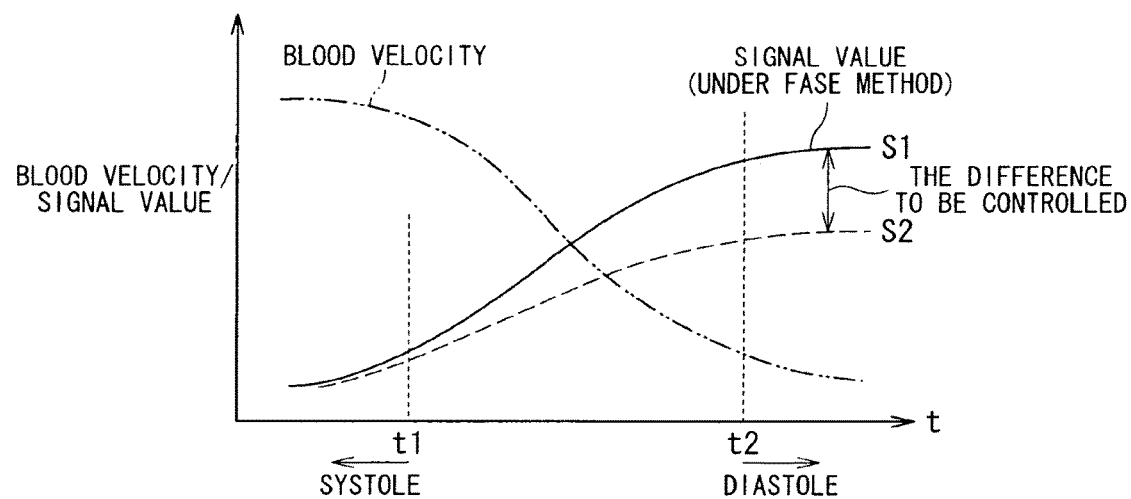
FIG. 12 is a diagram explaining effect and how to set each intensity of the Partial FC pulse and the Partial FS pulse shown in FIGS. 10 and 11 respectively.

FIG. 12 is a diagram explaining effect and how to set each intensity of the Partial FC pulse and the Partial FS pulse shown in FIGS. 10 and 11 respectively.

In FIG. 12, the ordinate denotes a blood velocity and relative signal value, and the abscissa denotes time from an R wave of an ECG signal. Further in FIG. 12, the dashed line denotes a temporal variation of blood velocity and the dotted line denotes a temporal variation of signal value of data acquired from a blood flow by an FASE sequence.

As shown in FIG. 12, in the systole before a time t1, although the velocity of the blood flow is relatively fast, the signal intensity obtained from the blood flow is relatively small. Meanwhile, in the diastole after the time t2, although the velocity of the blood flow is relatively slow, the signal intensity obtained from the blood flow is relatively high. This means a signal intensity varies depending on a time from an R wave of an ECG signal.

When a partial FC pulse and/or a partial FS pulse are applied, phase dispersion of magnetization spin is suppressed or promoted, and thus a time variation of a signal value changes. For example, the time variation S1 of the signal value shown as a solid line changes into the time variation S2 of the signal value shown as a dotted line. In other words, adjusting intensity of a partial FC pulse and/or a partial FS pulse can control a signal value obtained from a blood flow. Consequently, when a partial FC pulse and/or a partial FS pulse are applied with changing their intensity every one shot depending on a velocity of a blood flow and/or a delay time, each piece of data can be acquired in equivalent signal intensity at a different cardiac time phase.

Each intensity (or each waveform area) of a partial FC pulse and a partial FS pulse can be determined for every imaging portion by acquiring data on a trial basis in advance. It is acceptable to display each intensity of a partial FC pulse or a partial FS pulse determined as a default on a setting window of the display unit 34 once, and to enable a user to change it arbitrarily through operation of the input device 33.

When K-space data is acquired by a pulse sequence like this, the acquired K-space data, except for data by the last data acquisition of nth that acquires data in the low-frequency region and the high-frequency region, becomes data only in the low-frequency region.

Figure 13:
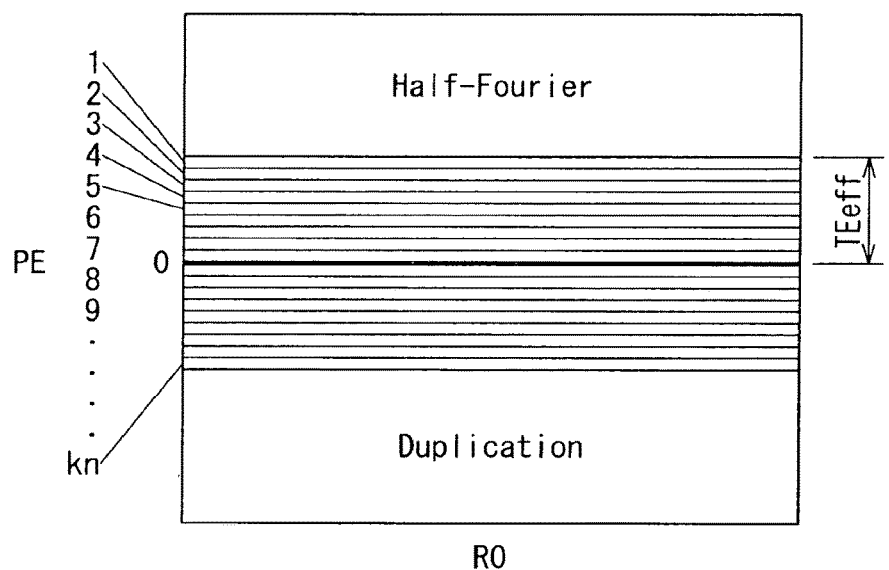
FIG. 13 is a diagram showing k-space data obtained in case of performing data acquisition with the FASE sequence shown in FIG. 9.

FIG. 13 is a diagram showing k-space data obtained in case of performing data acquisition with the FASE sequence shown in FIG. 9.

In FIG. 13, the abscissa denotes an RO direction and the ordinate denotes a PE direction. The K-space data as shown in FIG. 13 is acquired per one shot. Since the Half-Fourier method is used in an FASE sequence, the K-space data of a high-frequency region in the positive direction is not acquired. The K-space data of a low-frequency region in the positive direction is acquired by the data acquisition until the effective echo time TEeff and the K-space data of a low-frequency region in the negative direction is acquired by the data acquisition after the effective echo time TEeff.

The copy of the data, of a high-frequency region, acquired by the nth data acquisition is used as the K-space data of a high-frequency region in the negative direction that is necessary for image reconstruction but is not acquired.

This means the K-space data of a low-frequency region critical for the improvement of contrast is acquired per heart beat, and the K-space data of a high-frequency region is acquired at least once then shared between pieces of data acquired in the respective shots.

As described above, the number kn of lines of the K-space data in a PE direction can be determined as the number making it possible to obtain enough contrast by a test of imaging in advance. Alternatively, a range of K-space data to be acquired may be displayed on a setting window of the display unit 34 so that a user can change it through operation of the input device 33.

An example of setting an imaging condition for a two-dimensional Time-resolved MRDSA image has been described so far. However, the imaging condition for the two-dimensional Time-resolved MRDSA image can be used as an imaging condition of an ECG-prep scan that is a preparation scan for acquiring an optimum delay time from an R wave of an ECG signal.

When an ECG-prep scan is performed, a signal value of data from a blood flow per delay time from an R wave can be acquired. Consequently, a graph relating the delay times to the signal values of the data can be displayed so that a range of delay times for imaging an MRDSA image and the number of time phases (delay times) can be determined with reference to the graph. A graph relating the delay times to the signal values of data can be generated according to the following procedure (algorithm).

First, multiple ECG-prep images each corresponding to a mutually different delay time are generated by an ECG-prep scan. Any one of the multiple ECG-prep images is assumed to be the reference image, and then a difference between each ECG-prep image and the reference image is obtained. Alternatively a difference between two ECG-prep images out of multiple ECG-prep images is obtained with regard to all combinations. This generates multiple subtraction images. Then, an MIP image is generated by MIP processing to multiple subtraction images. Then, a mask image is generated by binarizing the MIP image and subsequently the generated mask image is multiplied by each of the multiple ECG-prep images. This enables an amount of characteristic regarding each delay time (time phase) to be calculated. Then, a graph relating each delay time to the amount of characteristic calculated in this way can be generated.

When a graph relating delay times to signal values of data is displayed for setting of imaging conditions and/or display conditions, the interface unit 41 is configured to obtain necessary data from another component such as the real space database 47, generate graph information expressing the graph relating the graph information on the display unit 34. Further, a graph range is specified through operation of the input device 33, and then the interface unit 41 provides instruction of an imaging range and/or a display range based on the specified graph range to the imaging condition setting unit 42 and the display processing unit 49.

By referencing the graph, a range of delay times for imaging an MRDSA image can be specified. For example, an imaging range can be set in a time phase, with signal variation, from a systole to a diastole of a heart. Specifically, an imaging range can be regarded as a range in which a delay time from an R wave of an ECG signal is from 200 ms to 350 ms.

Moreover, in addition to an imaging range, a variation width of a delay time and/or a repetition frequency of data acquisition also become targets for setting as mentioned above. FIG. 6 shows an example of setting window that specifies an initial value of a delay time, a variation width of the delay time and a frequency of data acquisition through operation of the input device 33. However, a variation width of a delay time and/or a repetition frequency of data acquisition may be calculated automatically by the computer 32 according to conditions. For example, if a range of delay times for imaging is specified, by specifying a reference delay time (an initial vale of a delay time, for example) Delay and a variation width Increment of a delay time through operation of the input device 33, the computer 32 can automatically calculate a repetition frequency of data acquisition and an imaging time. For another example, when an imaging time is specified through operation of the input device 33, the computer 32 can automatically calculate a reference delay time Delay and a variation width Increment of a delay time so that the data acquisition of the specified imaging range is completed within the specified imaging time. The repetition frequency of data acquisition, the imaging time, the reference delay time Delay and the variation width Increment of the delay time, obtained by these calculations or specified, can be displayed on the display unit 34 for reference.

Note that, since an ECG-prep scan is a preparation scan performed to determine an appropriate delay time, a variation width of a delay time for an MRDSA image is ordinarily set shorter than that between respective pieces of image data obtained by the ECG-prep scan.

Further, when a graph relating delay times concerning an MRDSA image to signal values of data is displayed, a range of delay times and the number of time phases (delay times) for displaying a blood flow image can also be determined.

Meanwhile, an imaging condition with echoshare for imaging a three-dimensional Time-resolved MRDSA image can also be set.

Figure 14:
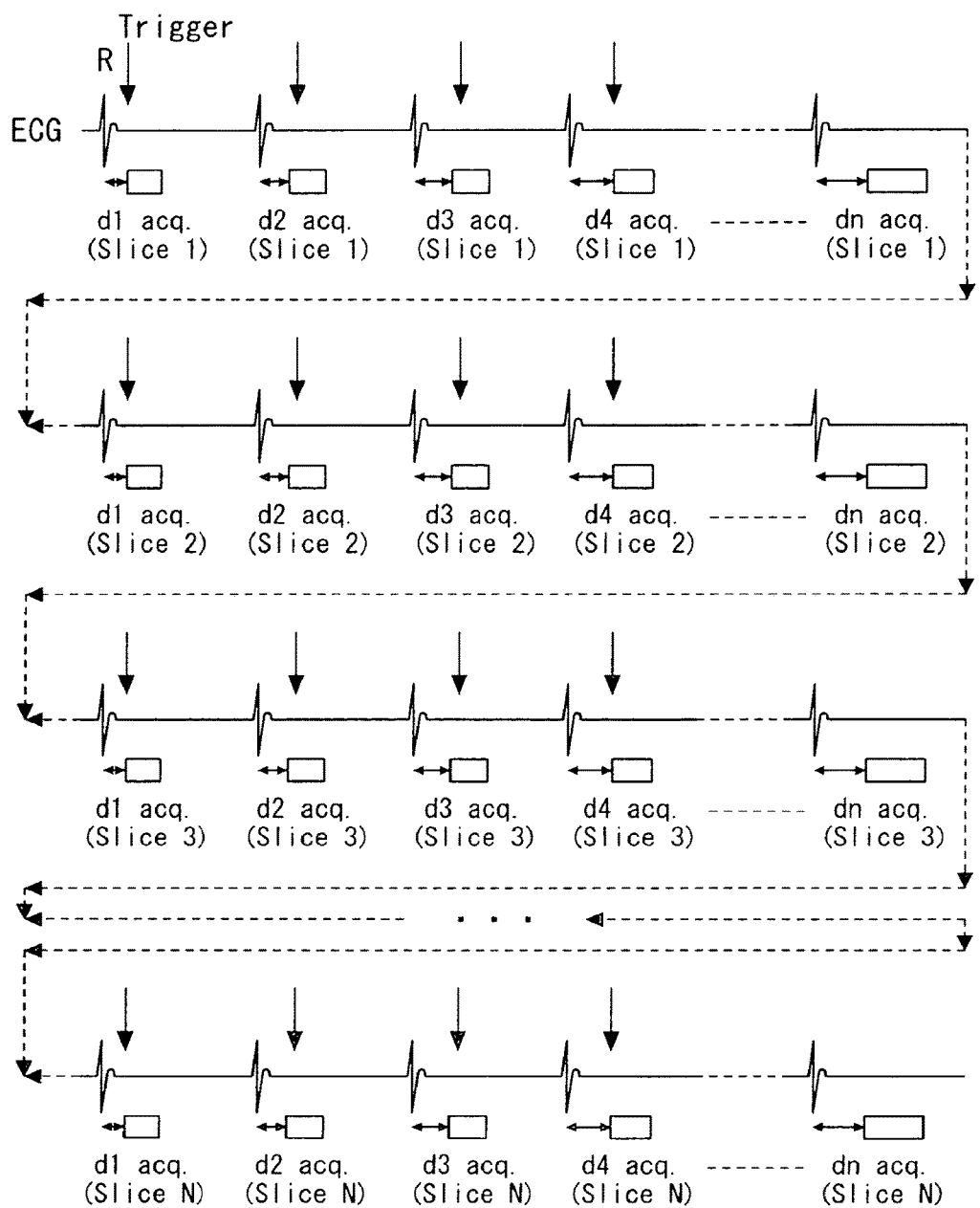
FIG. 14 is a diagram showing delay times and data acquisition periods in case of performing data acquisition for selecting the echo share mode on the setting window shown in FIG. 6 and generating a three-dimensional Time-resolved MRDSA image by a three-dimensional pulse sequence.

FIG. 14 is a diagram showing delay times and data acquisition periods in case of performing data acquisition for selecting the echo share mode on the setting window shown in FIG. 6 and generating a three-dimensional Time-resolved MRDSA image by a three-dimensional pulse sequence.

As shown in FIG. 14, data acquisition at a slice S1 can be performed similarly to two-dimensional data acquisition shown in FIG. 7. Specifically, data in the high-frequency region and the low-frequency region in the last data acquisition of nth at the slice S1 is acquired while data only in the low-frequency region is acquired in the other data acquisition. In a similar way, three-dimensional data can be acquired by two-dimensional data acquisition with echoshare repeated for every slice. In other words, each data acquisition for the slices S2, S3, . . . , Sn is performed similarly to the data acquisition for the slice S1. This allows to acquire three-dimensional echo data in a short time and generate a three-dimensional Time-resolved MRDSA image.

An imaging time can be reduced by selecting the echoshare mode as mentioned above on a setting window of an imaging condition.

Moreover, when the imaging mode by PI is selected on a setting window of an imaging condition, an imaging time can be reduced further. PI is a technique for acquiring data by skipping at least one phase encode with multiple surface coils 24c as described above. Therefore, the number of phase encodes can be reduced to a value obtained by multiplying a reciprocal of the number of surface coils 24c by the number of a phase encodes necessary for image reconstruction. Then, pieces of image data corresponding to the respective surface coils 24c are reconstructed from pieces of echo data received simultaneously by the respective surface coil 24c.

However, folding occurs in each piece of reconstructed image data for the respective surface coils 24c by PI. Therefore, unfolding processing is performed to each of the respective pieces of image data to remove folding by utilizing each sensitivity distribution of the surface coils 24c. Then conclusive image data for displaying is generated by combining the pieces of image data for the respective surface coils 24c after unfolding processing.

When imaging by moving table method or stepping-table method, instruction to set a condition such as positional information and an amount of step of the bed 37 is provided from the input device 33 to the interface unit 41 as an imaging condition.

When the instruction of the imaging condition as mentioned above is provided from the input device 33 to the interface unit 41 through the setting window displayed on the display unit 34, the corresponding information is provided form the interface unit 41 to the respective components. For example, application information of the echoshare mode and/or PI, the number of the surface coil 24c, the selected pulse sequence, the delay time and the number of shots are provided to the imaging condition setting unit 42. Further, application information of the echoshare mode, the pulse sequence, the delay time, the number of shots and application information of PI are provided to the image reconstruction unit 45, and application information of PI and the number of the surface coil 24c are provided to the unfolding processing unit 46, respectively.

Then, the image condition setting unit 42 sets imaging conditions according to the information obtained from the interface unit 41 and provides them to the sequence controller control unit 43.

Next in the step S2, an image processing method and an image displaying method are set through a setting window of an image processing condition and an image displaying condition displayed on the display unit 34. As shown in the upper right portion in FIG. 6, the auto subtraction processing mode serving as an image processing method can be selected so as to perform subtraction processing automatically for generating an MRDSA image. When selecting the auto subtraction mode, subtraction processing between pieces of image data is performed automatically to generate an MRDSA image without additionally providing instruction of subtraction processing to the interface unit 41 after the beginning of imaging.

For example, when a three-dimensional sequence is selected as a pulse sequence for data acquisition, the auto-MIP processing mode can be selected so as to perform MIP processing automatically. If the auto-MIP processing mode is selected, MIP processing to three-dimensional image data generated as MRDSA data is performed automatically to generate blood flow image data for displaying without providing instruction of MIP processing to the interface unit 41 separately after the beginning of imaging.

In addition, when a three-dimensional sequence is selected as a pulse sequence for data acquisition, a displaying method of multiple pieces of MIP image data generated as blood flow image data for displaying can be set as shown in the lower right portion in FIG. 6.

Figure 15:
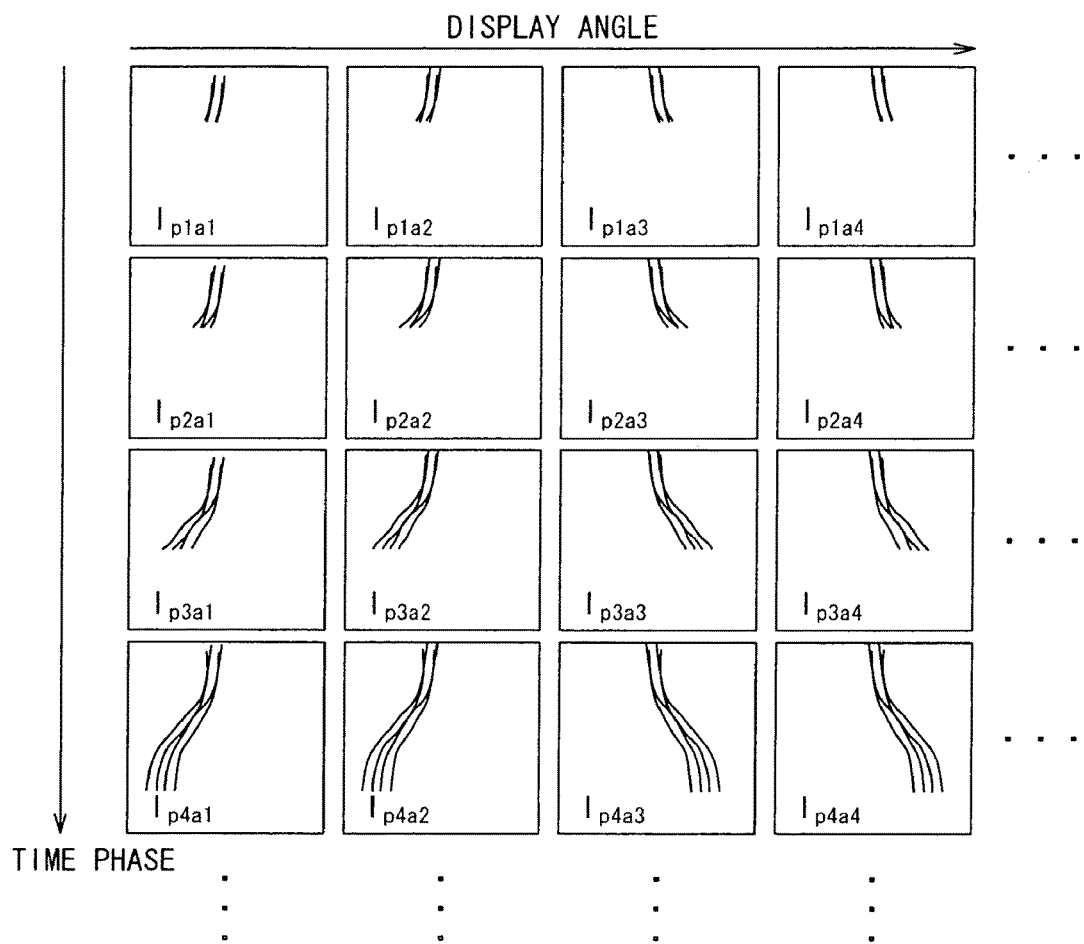
FIG. 15 is a diagram explaining an order for displaying MIP images which is set on the setting window shown in FIG. 6.

FIG. 15 is a diagram explaining an order for displaying MIP images which is set on the setting window shown in FIG. 6.

In FIG. 15, the abscissa denotes a display angle representing a projection direction for MIP images and the ordinate denotes time phase. The images laid out as shown in FIG. 15 are MIP images for displaying acquired by a three-dimensional scan. In FIG. 15, a display angle of an MIP image changes toward in the abscissa axis direction, and the time elapses and blood on an MIP image flows gradually toward in the ordinate axis direction.

When Phase/Swing is selected as an image displaying method, the MIP images are displayed on the display unit 34 in the image display method for displaying MIP images corresponding to mutually different time phases sequentially, and subsequently displaying MIP images from another display angle with elapse of time phase sequentially after. Specifically, the MIP images are displayed on the display unit 34 in the order of Ip1a1, Ip2a1, Ip3a1, . . . , Ip1a2, Ip2a2, Ip3a2, . . . , Ip1a3, Ip2a3, Ip3a3, . . . . On the other hand, when Swing/Phase is selected as an image displaying method, the MIP images are displayed on the display unit 34 in the image displaying method for displaying MIP images with gradually changing a display angle sequentially, and subsequently displaying MIP images in the next time phase with gradually changing a display angle. Specifically, the MIP images are displayed on the display unit 34 in the order of Ip1a1, Ip1a2, Ip1a3, . . . , Ip2a1, Ip2a2, Ip2a3, . . . , Ip3a1, Ip3a2, Ip3a3, . . . .

In addition, a direction of projection for generating an MIP image can be set as an image displaying method. For example, the number of projection directions can be specified and projection planes obtained by evenly dividing the angle of 180 degrees by the specified number can be set as the projection direction. Moreover, a displaying time of one MIP image can be set. For example, when the scroll bar is scrolled to the minus side in FIG. 6, a displaying speed of MIP images slows down and the MIP images are displayed in slow motion. On the contrary, when the scroll bar is scrolled to the plus side, the MIP images are run with fast-forward.

In addition, when imaging by the moving table method or the stepping-table method, an image displaying method of a blood flow image data can be set according to each position of the bed 37. In this case in connection with an image displaying method, when an imaging condition is set so that mutually corresponding pieces of data between plural portions serving as imaging targets in positions of the bed 37 are acquired with the same delay time, blood flow image data can be displayed effectively.

For example, when blood flow image data is for a moving image, the blood flow image data can be displayed with matching time phases between pieces of blood flow image data from respective positions.

Figure 16:
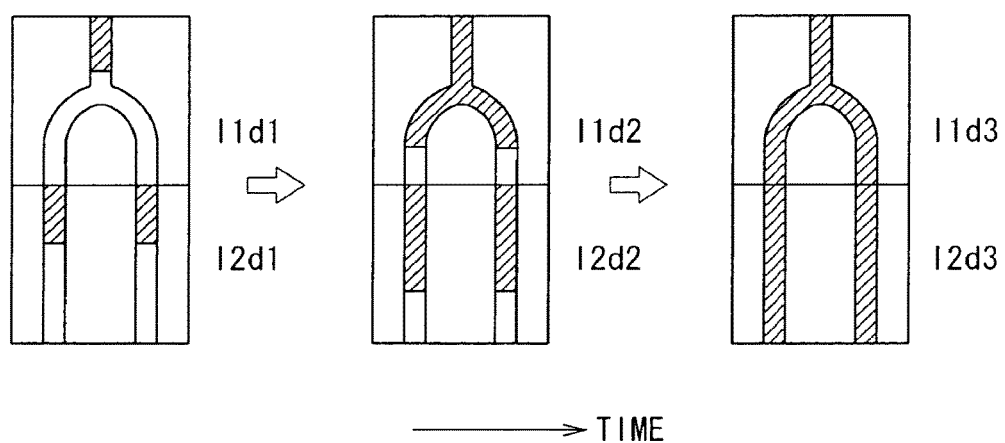
FIG. 16 is a diagram explaining a method for displaying pieces of blood flow image data corresponding to two parts respectively with matching time phases when the pieces of blood flow image data are obtained with moving the bed 37.

FIG. 16 is a diagram explaining a method for displaying pieces of blood flow image data corresponding to two parts respectively with matching time phases when the pieces of blood flow image data are obtained with moving the bed 37.

As shown in FIG. 16, two pieces of blood flow image data can be connected and displayed in the time series. When time phases d1, d2, d3, . . . of the respective pieces of blood flow image data I1 and I2 are mutually set to be same or near, the blood flow image data can be displayed as if blood is flowing in each of the blood flow images I1d1, I1d2, I1d3, . . . , I2d1, I2d2, I2d3, . . . .

Figure 17:
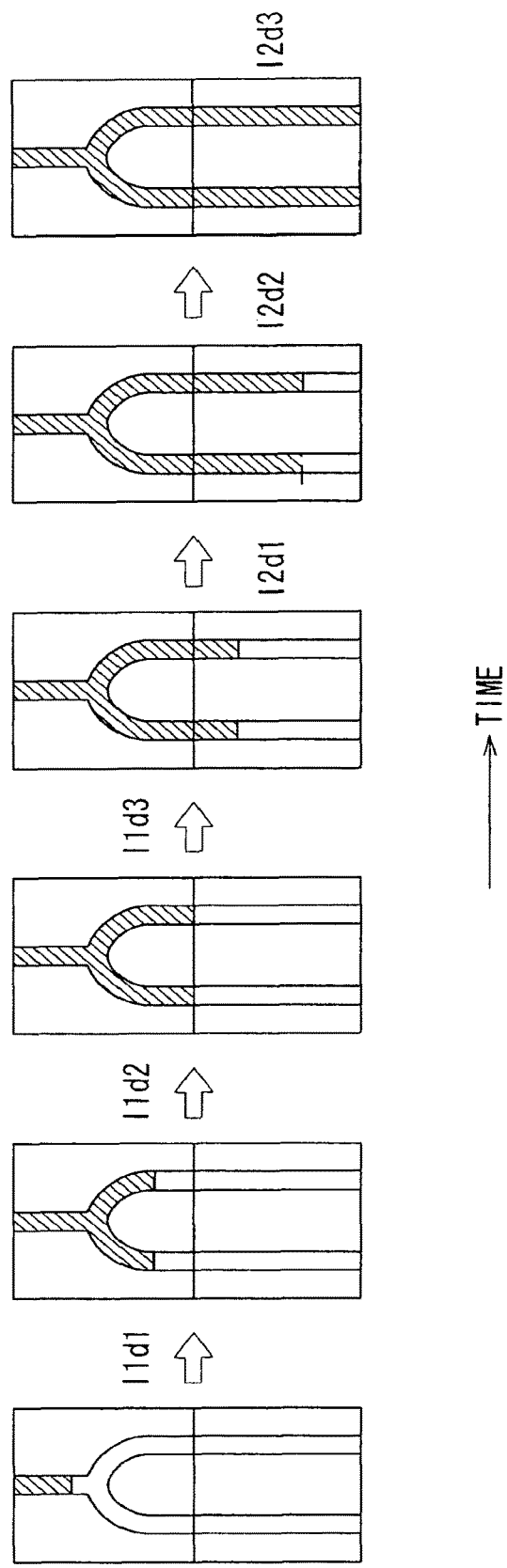
FIG. 17 is a diagram explaining a method for displaying image data of upstream side corresponding to the last time phase and subsequently image data of the adjacent downstream side corresponding to the first time phase according to a direction of blood flow when the pieces of blood flow image data corresponding to two parts respectively are obtained with moving the bed.
Figure 18:
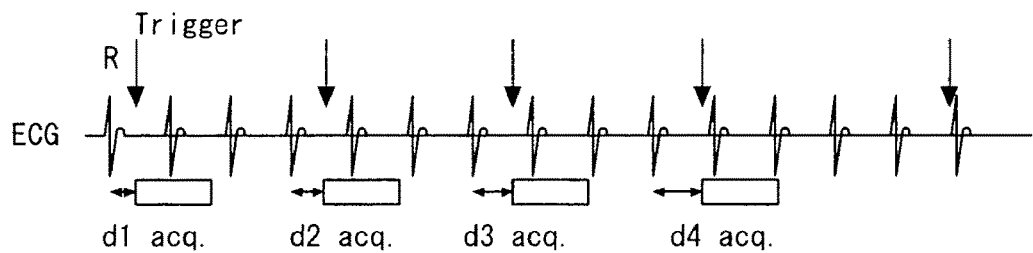
FIG. 18 is a diagram showing a conventional imaging scan with use of an ECG-prep scan.
Figure 19:
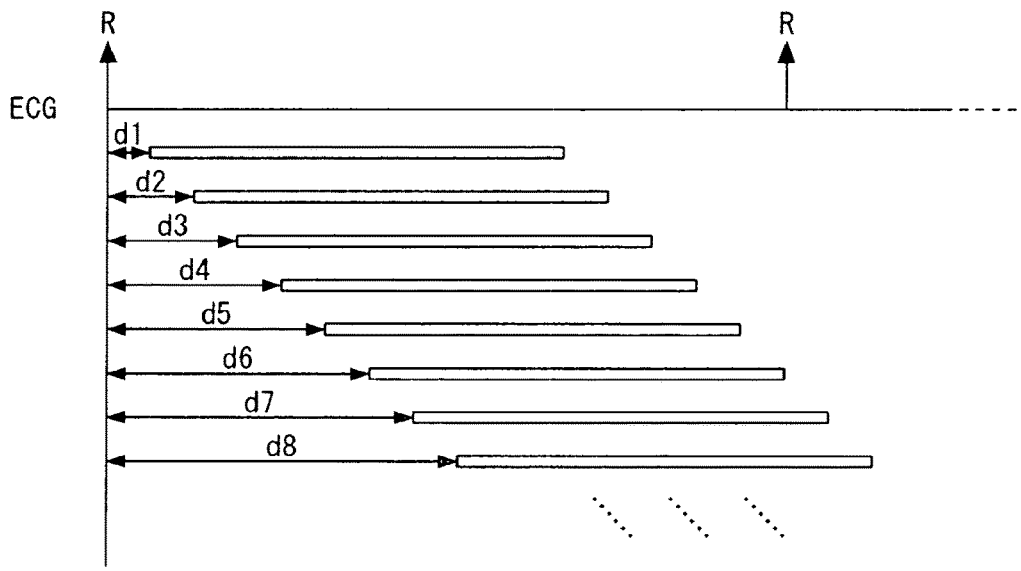
FIG. 19 is a diagram showing delay times from an R wave of an ECG signal for respective acquisition timings of pieces of image data acquired by the imaging scan shown in FIG. 18.

FIG. 17 is a diagram explaining a method for displaying image data of upstream side corresponding to the last time phase and subsequently image data of the adjacent downstream side corresponding to the first time phase according to a direction of blood flow when the pieces of blood flow image data corresponding to two parts respectively are obtained with moving the bed 37.

As shown in FIG. 17, two pieces of blood flow image data I1 and I2 can be connected and displayed in the time series. When displaying the downstream blood flow image data I2d1 corresponding to the initial time phase d1 after displaying the upstream blood flow image data I1d3 corresponding to the last time phase d3, the blood flow image data can be displayed as if blood is flowing continuously between two parts.

Information indicating an image displaying method and an image processing method that are thus set up is provided from the interface unit 41 to the blood flow image generating unit 48 as a blood flow image to be generated, and information indicating the image displaying method is also provided to the display processing unit 49.

After completing setting of the imaging condition, the image processing method and the image displaying method, an object P is set on the bed 37. Further, a static magnetic field is generated in an imaging area in the static field magnet 21 (superconducting magnet) excited in advance by the static magnetic field power supply 26. An electric current is supplied from the shim coil power supply 28 to the shim coil 22 to uniform the static magnetic field generated in the imaging area. The imaging condition, the image processing method and the image displaying method may be set collectively, not separately.

Then in step S3, data acquisition is performed. Specifically, instruction to start a scan is provided through the interface unit 41 from the input device 33 to the sequence controller control unit 43. Then, the sequence controller control unit 43 provides a pulse sequence such as an FASE sequence acquired from the imaging condition setting unit 42 to the sequence controller 31. The sequence controller 31 generates a gradient magnetic field in the imaging area where the object P is set by driving the gradient power supply 27, the transmitter 29 and the receiver 30 according to the pulse sequence received from the sequence controller control unit 43 and also generates a radio frequency signal from the RF coil 24.

Consequently, an NMR signal generated by the nuclear magnetic resonance in the object P is received by the RF coil 24 and provided to the receiver 30. The receiver 30 performs necessary signal processing in response to the NMR signal from the RF coil 24, and then generates raw data that is an NMR signal of digital data by A/D conversion. The receiver 30 provides the generated raw data to the sequence controller 31. The sequence controller 31 provides the raw data to the sequence controller control unit 43 and the sequence controller control unit 43 arranges the raw data as K-space data in the K-space formed in the K-space database 44.

The data acquisition like this is performed in synchronization with an ECG according to an ECG signal of the object P acquired by the ECG unit 38. That is to say, following triggers set so as to increase a delay time gradually from an R wave of the ECG signal, pieces of data corresponding to the number of shots specified through the setting window shown in the FIG. 6 are acquired. The delay time increases by the increment value, depending on the number of shots, from the initial delay time set in the setting window in the FIG. 6.

In the echoshare mode, K-space data of a low-frequency region is acquired in each shot other than the nth shot and arranged in the K-space database 44 while K-space data of a low-frequency region and a high-frequency region is acquired in the nth shot and arranged in the K-space database 44. Therefore, the data can be acquired in a short time and data for one shot can be acquired in one heart beat. When the imaging mode by PI is selected, since data is acquired by the specified number of the surface coils 24c with skipping the number of phase encodes, data acquisition time is reduced further. Consequently, sufficient time can be reserved for T1 recovery between the end of data acquisition and the next R wave.

Then in step S4, the image reconstruction unit 45 generates image data from K-space by retrieving the K-space data from the K-space database 44 and performing image reconstruction processing such as Fourier transform processing to the K-space data. Note that, a copy of the K-space data of the high-frequency region acquired in the nth data acquisition is used as deficient K-space data, of the high-frequency region in the K-space in the negative direction, among the K-space data acquired in each data acquisition other than nth. Further, the deficient K-space data of the high-frequency region in the positive direction in the K-space is calculated based on the complex conjugate relation under the Half-Fourier method. When the K-space is filled with the copy of data and by the complex conjugate calculation, the image data is generated by image reconstruction processing.

When a notice of the imaging mode by PI from the interface unit 41 is not provided, the image reconstruction unit 45 writes the image data obtained by reconstruction on the real space database 47. On the contrary, when a notice of the imaging mode by PI from the interface unit 41 is provided, the image reconstruction unit 45 provides the pieces of image data, corresponding to the respective surface coils 24c, obtained by reconstruction to the unfolding processing unit 46.

The unfolding processing unit 46 generates unfolded image data by performing unfolding processing on the image data from each surface coil 24c obtained from the image reconstruction unit 45. At this time, each sensitivity distribution of corresponding surface coils 24c stored in the sensitivity distribution database 40 is referred to by the unfolding processing unit 46 and used for unfolding processing. In addition, a condition such as the number of the surface coils 24c and NOWRAP obtained from the interface unit 41 is also used for unfolding processing. Then, the unfolding processing unit 46 writes the generated image data on the real space database 47.

Then in step S5, according to the instruction from the interface unit 41, the blood flow image generating unit 48 obtains multiple pieces of image data corresponding to mutually different cardiac time phases stored in the real space database 47 and generates blood flow image data for displaying. For example, the blood flow image generating unit 48 generates Time-resolved MRDSA image data by subtraction processing between pieces of image data corresponding to mutually near time phase or between a reference image data and image data corresponding to each time phase.

When performing subtraction processing of the image data in each time phase to the reference image data, a timing corresponding to a delay time do from an R wave of the ECG signal is set in a diastole and image data acquired in the diastole can be considered to be the reference image data Idn. When performing subtraction processing between the image data Id1, Id2, Id3, . . . in each time phase, acquired at a timing corresponding to each delay time d1, d2, d3, . . . , and the reference image data Idn, subtraction image data Idn-Id1, Idn-Id2, Idn-Id3, . . . obtained as a result of subtraction processing becomes bright cine image data showing blood flow images.

This subtraction processing is performed automatically when the auto subtraction processing mode is selected in the setting window shown in the FIG. 6. On the contrary, when the auto subtraction processing mode is not selected, a user operates the input device 33 so that instruction of subtraction processing is provided to the blood flow image generating unit 48 through the interface unit 41.

Alternatively, the image data Id1, Id2, Id3, . . . in each time phase may be set as blood flow image data for displaying without subtraction processing, as it is. In this case, the blood flow image data for displaying becomes black cine image data.

When acquisition of two-dimensional image data for an ECG-prep is the purpose, no subtraction processing of time-resolved data is also necessary and therefore the image data generated by the image reconstruction unit 45 or the unfolding processing unit 46 can be used without modification.

When the auto-MIP processing mode is selected in the setting window shown in the FIG. 6, the three-dimensional Time-resolved MRDSA image data after subtraction processing is automatically subjected to MIP processing toward a specified projection plane.

The two-dimensional Time-resolved MRDSA image data and the MIP image data generated by this means are provided as blood flow image data from the blood flow image generating unit 48 to the display processing unit 49.

Then in step S6, the display processing unit 49 performs display processing to the blood flow image data according to the instruction from the interface unit 41 so that the blood flow image data can be displayed on the display unit 34 in the displaying order and the displaying time set in the setting window, and outputs the processed blood flow image data to the display unit 34. As a result, a blood flow image is displayed on the display unit 34. When the three-dimensional Time-resolved MRDSA image data is especially generated, multiple MIP images are sequentially displayed in a displaying method instructed as Phase/Swing or Swing/Phase.

When imaging by the moving table method or the stepping-table method has been performed, pieces of blood flow image data corresponding to the respective positions of the bed 37 are mutually connected. The respective pieces of blood flow image data can be displayed with matching their time phases, and alternatively can be displayed continuously so that the initial time phase in the downstream side can come after the last time phase in the upstream side.

That is to say, the magnetic resonance imaging apparatus 20 as mentioned above is an apparatus which can acquire data in a short time using the echoshare technique and/or PI so that image data of a single slice and multi phases can be acquired effectively. The image data of a single slice and multi phases is aimed at non-contrast-enhanced Time-resolved MRDSA image data and image data acquired by an ECG-prep.

According to the echoshare technique, it is only necessary to perform data acquisition of only low-frequency components in the K-space several times, and perform data acquisition of high-frequency components in the K-space at least once. This can reduce an imaging time per shot. Moreover, an imaging time can be reduced further in combination with PI. Consequently, data can be acquired with a TR as one heart beat (1RR). It is suitable to use an FASE sequence that can acquire data in a shorter time. At this time, data can be acquired with a stable signal value by applying a Partial FC pulse and/or a Partial FS pulse according to a velocity of a blood flow.

Furthermore, if the echoshare technique and/or PI are applied to a three-dimensional non-contrast-enhanced Time-resolved MRDSA, three-dimensional blood flow function, which is DSA information in a slice direction, can be measured in a short time. Consequently, according to the magnetic resonance imaging apparatus 20, imaging of non-contrast-enhanced Time-resolved MRDSA image as functional imaging can be performed in a shorter time.

In addition, configuration of an interface so that subtraction processing and/or MIP processing are automatically performed to the reconstructed image data can reduce work of a user. At the same time, by providing with an interface in consideration of user's convenience, an MIP image in each time phase and to each projection direction can be automatically and sequentially displayed in a displaying order and a displaying speed specified in advance without the user's operation when MIP images are generated in multiple directions by three-dimensional imaging. This continuous automatic display of MIP images in time series toward multiple projection directions can be performed on blood flow images with contrast medium and/or images other than blood flow images as well as on non-contrast-enhanced blood flow images. An interface can be configured so that auto subtraction processing and/or automatic projection processing can be performed in a three-dimensional Time-resolve MRDSA without the echoshare technique and/or PI.

Moreover, with the echoshare technique, a method of generating an image using pieces of data acquired in a certain heart beat and in another heart beat respectively can also be used for generating not only a non-contrast-enhanced blood flow image but a blood flow image with contrast medium and a diagnostic image other than a blood flow image. In combination with PI, this method can be applied to generation of various diagnostic images including a non-contrast-enhanced blood flow image and a blood flow image with contrast medium as well.

Meanwhile, the magnetic resonance imaging apparatus 20 as mentioned above generates image data in the state where K-space data is filled by using a copy of K-space data in a high-frequency region according to the echoshare technique and performs subtraction processing of the generated image data. However, the magnetic resonance imaging apparatus 20 can also generate image data once from K-space data consisting of only low-frequency components for subtraction processing and perform complementary processing, as display processing, of a part corresponding to a high-frequency component to subtraction image data acquired as blood flow image data before displaying the subtraction image data. In this case, complementary processing to the blood flow image data can be performed by the display processing unit 49. In this way, when a copy of a high-frequency component is used as complementary data after subtraction processing, blood flow image data can be also obtained with high resolution.

In addition, an image processing apparatus can be configured to have image processing functions, such as the subtraction processing and projection processing, of the magnetic resonance imaging apparatus 20 as mentioned above and representational function of various image data. An image processing apparatus can be built in a PACS (picture archiving and communication system) for example, and can connect to the magnetic resonance imaging apparatus 20 via networks. In this case, part of the image processing function and/or the representational processing function can be omitted from the magnetic resonance imaging apparatus 20. However, if both of the magnetic resonance imaging apparatus 20 and the image processing apparatus have the image processing function and the representational processing function, a blood flow image can be displayed as a moving image or a still image in a various displaying method on both of the magnetic resonance imaging apparatus 20 and the image processing apparatus.

What is claimed is:

1. A magnetic resonance imaging (MRI) apparatus comprising:
   an assembly of MRI gantry components including static and gradient magnetic field generators and at least one radio frequency (RF) coil defining an imaging volume;
   an MRI control system, connected to control said gantry components, including at least one RF transmitter, at least one RF receiver and at least one controlling computer having an operator input and display configured to:
      effect specified MRI data acquisition sequences of RF and gradient magnetic pulses which acquire, from an object located within said imaging volume, RF nuclear magnetic resonance (NMR) spin responses emanating from different spatially located volumes of NMR nuclei respectively corresponding to different positions in k-space as a function of a magnetic field experienced by the NMR nuclei;
      perform a preparation scan to acquire signal values of a blood flow while changing delay times from an R wave in synchronization with an electrocardiogram, generate a graph which depicts the signal values of the blood flow acquired by the preparation scan and the delay times, accept a range of the delay times for a main scan which acquires data for generating non-contrast-enhanced time-resolved MRDSA (Magnetic Resonance Digital Subtraction Angiography) images, the range of the delay times being input by an operator referencing the graph, perform the main scan based on the range of the delay times in synchronization with an electrocardiogram, and generate, from the data acquired by the main scan, non-contrast-enhanced time-resolved MRDSA images representing a dynamic state of blood flow.

2. The magnetic resonance imaging apparatus of claim 1, wherein the at least one controlling computer is configured to acquire data for generating three or more non-contrast-enhanced time-resolved MRDSA images having delay times different from each other.

3. The magnetic resonance imaging apparatus of claim 1, wherein the at least one controlling computer is configured to display the graph.

4. A method of generating non-contrast-enhanced time-resolved MRDSA (Magnetic Resonance Digital Subtraction Angiography) images, the method comprising:

performing a preparation scan with a magnetic resonance imaging (MRI) system to acquire signal values of a blood flow while changing delay times from an R wave in synchronization with an electrocardiogram, generating a graph which depicts the signal values of the blood flow acquired by the preparation scan and the delay times, accepting a range of the delay times for a main scan which acquires data for generating non-contrast-enhanced time-resolved MRDSA (Magnetic Resonance Digital Subtraction Angiography) images, the range of the delay times being input by an operator referencing the graph, performing the main scan with the MRI system based on the range of the delay times in synchronization with an electrocardiogram, and generating, from the data acquired by the main scan, non-contrast-enhanced time-resolved MRDSA images representing a dynamic state of blood flow.

\* \* \* \* \*